United States Patent [19]

Kim et al.

[11] Patent Number: 5,726,127
[45] Date of Patent: Mar. 10, 1998

[54] THIOPHENESULFONYLUREA DERIVATIVES AND HERBICIDAL COMPOSITION CONTAINING THE SAME

[75] Inventors: Dae Whang Kim; Kyeong Yeol Yun; Jae Wook Ryu; Yeon Soo Lee; Seung Kyu Kang; In Taek Hwang, all of Daejeon, Rep. of Korea

[73] Assignee: Korea Research Institute of Chemical Technology, Daejeon, Rep. of Korea

[21] Appl. No.: 646,352

[22] PCT Filed: Nov. 9, 1994

[86] PCT No.: PCT/KR94/00161

§ 371 Date: Jul. 24, 1996

§ 102(e) Date: Jul. 24, 1996

[87] PCT Pub. No.: WO95/13276

PCT Pub. Date: May 18, 1995

[30] Foreign Application Priority Data

Nov. 10, 1993 [KR] Rep. of Korea .................. 93-23890

[51] Int. Cl.$^6$ .................................................. A01N 47/36
[52] U.S. Cl. ...................... 504/239; 504/230; 504/243; 544/320; 544/331; 544/212; 549/65
[58] Field of Search .............................. 544/320, 331, 544/212; 504/230, 243, 239; 549/65

[56] References Cited

U.S. PATENT DOCUMENTS

| 4,929,637 | 5/1990 | Baldwin et al. | 514/445 |
| 5,300,499 | 4/1994 | Chow | 514/231.5 |

FOREIGN PATENT DOCUMENTS 0559044  2/1993  European Pat. Off. .

*Primary Examiner*—Brian M. Burn
*Attorney, Agent, or Firm*—Birch, Stewart, Kolasch & Birch, LLP

[57] ABSTRACT

The present invention relates to a thiophenesulfonylurea derivative represented by general formula (I), the process for preparation thereof, and herbicide using it; and a salt thereof, in which T represents a group T1, T2, or T3 having general formulae (a), wherein E represents a direct bond; R represents hydrogen or $C_{1-4}$ acyl; $R^1$ represents $C_{1-6}$ alkyl substituted with 1 to 3 halogen atoms; $R^2$ represents hydrogen, $C_{1-3}$ alkyl, $C_{1-3}$ haloalkyl, halogen, cyano, $C_{1-3}$ alkoxy, $C_{1-3}$ haloalkoxy, amino, methylamino, dimethylamino, or $C_{1-3}$ alkyl substituted with $C_{1-2}$ alkoxy, $C_{1-2}$ haloalkoxy, thiol, methylthio, cyano or hydroxy; A represents a group selected from A1 to A4 having general formulae (b), and a herbicidal composition containing these derivatives.

15 Claims, No Drawings

THIOPHENESULFONYLUREA DERIVATIVES AND HERBICIDAL COMPOSITION CONTAINING THE SAME

This application is a 371 of PCT/KR94/00161 filed on Nov. 9, 1994.

TECHNICAL FIELD

The present invention relates to a novel thiophenesulfonylurea derivative represented by the following general formula (I):

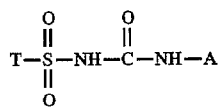
(I)

and a salt thereof, in which

T represents a group T1, T2, or T3 having the following general formula:

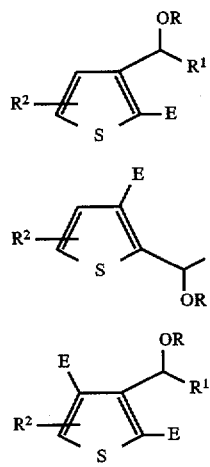

wherein

E represents a direct bond;

R represents hydrogen or $C_{1-4}$ acyl;

$R^1$ represents $C_{1-6}$ alkyl substituted with 1 to 3 halogen atoms;

$R^2$ represents hydrogen, $C_{1-3}$ alkyl, $C_{1-3}$ haloalkyl, halogen, cyano, $C_{1-3}$ alkoxy, $C_{1-3}$ haloalkoxy, amino methylamino, dimethylamino, or $C_{1-2}$ alkyl substituted with $C_{1-2}$ alkoxy, $C_{1-2}$ haloalkoxy, thiol, methylthio, cyano or hydroxy;

A represents a group selected from A1 to A4 having the following general formulae:

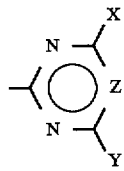

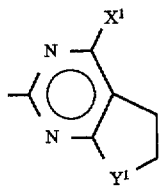

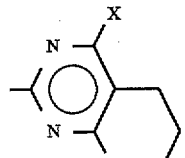

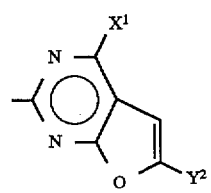

wherein

X represents hydrogen, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ haloalkylthio, halogen, $C_{2-5}$ alkoxyalkyl, $C_{2-5}$ alkoxyalkoxy, imino, $C_{1-3}$ alkylamino, di($C_{1-3}$ alkyl) amino or $C_{3-5}$ cycloalkyl;

$X^1$ represents $C_{1-2}$ alkyl, $C_{1-2}$ alkoxy or $C_{1-2}$ alkylthio;

Y represents hydrogen, $C_{1-4}$ alkyl, $C_{1-4}$ alkoxy, $C_{1-4}$ haloalkoxy, $C_{1-4}$ haloalkylthio, $C_{1-4}$ alkylthio, $C_{2-5}$ alkoxyalkyl, $C_{2-5}$ alkoxyalkoxy, amino, $C_{1-3}$ alkylamino, di($C_{1-3}$ alkyl)amino, $C_{3-4}$ alkenyloxy, $C_{3-4}$ alkynyloxy, $C_{2-5}$ alkylthioalkyl, $C_{1-4}$ haloalkyl, $C_{2-4}$ alkynyl, azido, cyano, $C_{2-5}$ alkylsulfinylalkyl, $C_{2-5}$ alkylsulfonylalkyl, hydroxymethyl, $C_{3-5}$ cycloalkyl or $C_{3-5}$ cloalkoxy;

$Y^1$ represents oxygen or methylene;

$Y^2$ represents hydrogen or methyl; and

Z represents N or CH; provided that (1) when X is fluoro, chloro/iodo, Z represents CH and Y represents methoxy, ethoxy, methoxymethylamino, amino, methylamino, dimethylamino or difluoromethoxy and (2) when X or Y is difluoromethoxy, Z represents CH and (3) when the total number of carbon atoms of X and Y is 4 or more, $R^2$ represents a group having up to 4 carbon atoms.

The present invention also relates to a process for preparation of the compound of formula (I), as defined above, and a herbicidal composition containing the compound (I) as an active ingredient.

BACKGROUND ART

In the prior art, numerous sulfonylurea derivatives have been well known as having herbicidal activity. For example, Korean Patent Application No. 91-3704 discloses a compound represented by the following general formula(A):

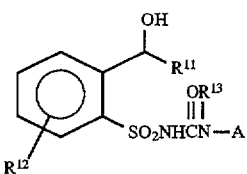

in which

R¹¹ represents $C_{1-6}$ alkyl substituted with 1 to 3 halogen atoms;

R¹² represents hydrogen, halogen, substituted alkyl group, substituted alkoxy group, etc.;

R¹³ represents hydrogen or methyl;

A represents a pyrimidine or triazine derivative.

In addition, Korean Patent Application No. 91-4063 discloses a compound represented by the following general formula (B):

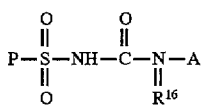

in which

P represents a group P1, P2 or P3 having the following general formula:

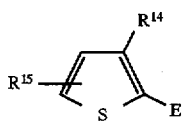

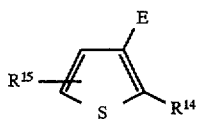

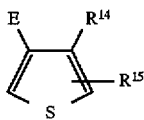

wherein

E represents $CH_2$ or a direct bond;

R¹⁴ represents

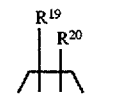

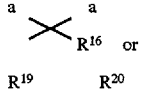

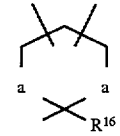

wherein,

R16 represents $C_{1-6}$ alkyl substituted with 1 to 3 halogen atoms,

R¹⁷ and R¹⁸ each independently represents $C_{1-4}$ alkyl,

R¹⁹ and R²⁰ each independently represents hydrogen, $C_{1-3}$ alkyl, or $C_{1-3}$ haloalkyl, and a represents O or S;

R¹⁵ represents hydrogen, halogen, substituted alkyl, etc.;

A represents a pyrimidine or triazine derivative.

However, those prior herbicidal sulfonylurea derivatives are undesirable due to their poor herbicidal activity and selectivity on undesirable weeds to be controlled.

Thus, the present inventors have extensively studied to develope an excellent herbicidal compound having herbicidal activity and selectivity on undesirable weeds to be controlled. As a result, we found that the compound of formula (I), as defined above, according to the present invention provide the desired potent herbicidal activity and selectivity and thus completed the present invention.

DISCLOSURE OF INVENTION

Accordingly, it is an object of the present invention to provide a novel thiophenesulfonylurea derivative represented by the following general formula (I):

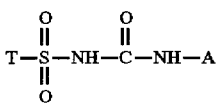

and a salt thereof, in which

T represents a group T1, T2 or T3 having the following general formula:

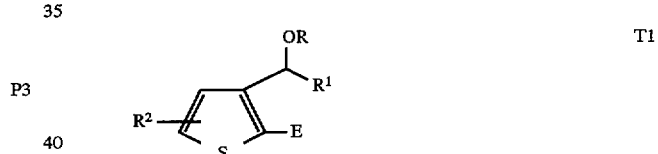

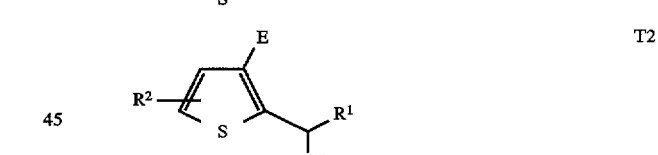

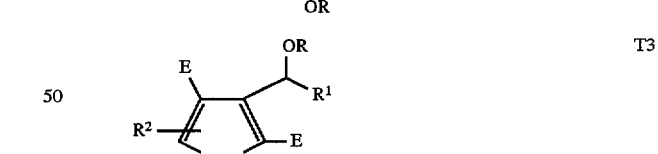

wherein

E represents a direct bond;

R represents hydrogen or $C_{1-4}$ acyl;

R¹ represents $C_{1-6}$ alkyl substituted with 1 to 3 halogen atoms;

R² represents hydrogen, $C_{1-3}$ alkyl, $C_{1-3}$ haloalkyl, halogen, cyano, $C_{1-3}$ alkoxy, $C_{1-3}$ haloalkoxy, amino, methylamino, dimethylamino, or $C_{1-2}$ alkyl substituted with $C_{1-2}$ alkoxy, $C_{1-2}$ haloalkoxy, thiol, methylthio, cyano or hydroxy;

A represents a group selected from A1 to A4 having the following general formulae:

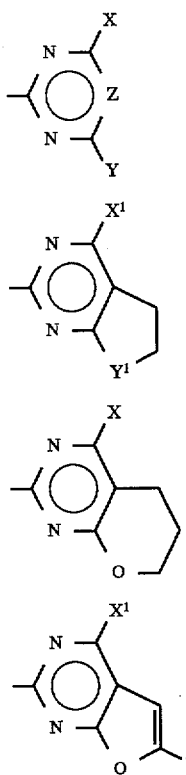

(A1)

(A2)

(A3)

(A4)

wherein

X represents hydrogen, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ haloalkylthio, halogen, $C_{2-5}$ alkoxyalkyl, $C_{2-5}$ alkoxyalkoxy, imino, $C_{1-3}$ alkylamino, di($C_{1-3}$ alkyl)amino or $C_{3-5}$ $X^1$ represents $C_{1-2}$ alkyl, $C_{1-2}$ alkoxy or $C_{1-2}$ alkylthio;

Y represents hydrogen, $C_{1-4}$ alkyl, $C_{1-4}$ alkoxy, $C_{1-4}$ haloalkoxy, $C_{1-4}$ haloakylthio, $C_{1-4}$ alkylthio, $C_{2-5}$ alkoxyalkyl, $C_{2-5}$ alkoxyalkoxy, amino, $C_{1-3}$ alkylamino, di($C_{1-3}$ alkyl)amino, $C_{3-4}$ alkenyloxy, $C_{3-4}$ alkynyloxy, $C_{2-5}$ alkylthioalkyl, $C_{1-4}$ haloalkyl, $C_{2-4}$ alkynyl, azido, cyano, $C_{2-5}$ alkylsulfinylalkyl, $C_{2-5}$ alkylsulfonylalkyl, hydroxymethyl, $C_{3-5}$ cycloakyl or $C_{3-5}$ cycloalkoxy;

$Y^1$ represents oxygen or methylene;

$Y^2$ represents hydrogen or methyl; and

Z represents N or CH;

provided that (1) when X is fluoro, chloro, iodo, Z represents CH and Y represents methoxy, ethoxy, methoxymethylamino, amino, methylamino, dimethylamino or difluoromethoxy and (2) when X or Y is difluoromethoxy, Z represents CH and (3) when the total number of carbon atoms of X and Y is 4 or more, $R^2$ represents a group having up to 4 carbon atoms.

It is another object of the present invention to provide a process for preparing the compound of formula (I) and a salt thereof as defined above, characterized in that (a) in order to prepare a compound of formula (I) wherein R is acyl, i.e. a compound of the following general formula (I-4), (i-5), or (I-6):

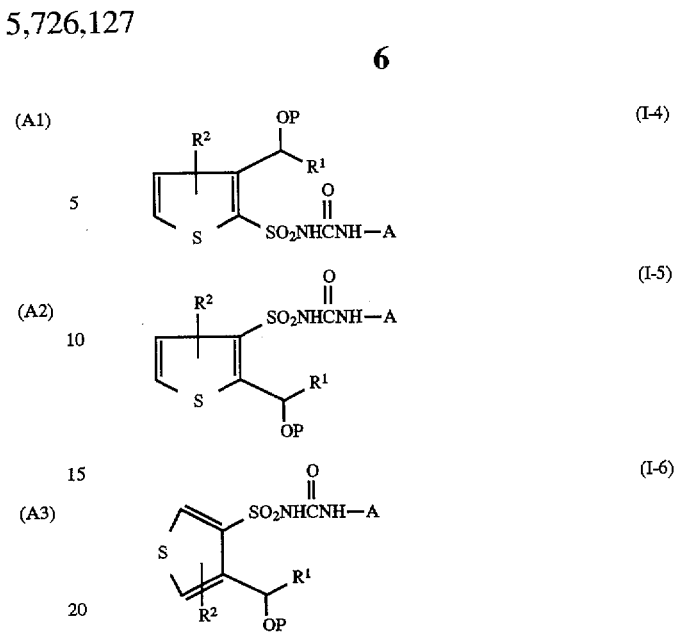

wherein $R^1$, $R^2$ and A are defined as previously described, and

P represents a protecting group which can be easily removed by an acid or an alkali hydrolysis or by any other method, preferably $C_{1-4}$ acyl and most preferably acetyl, a compound having the following general formula (II) corresponding to the desired product, i.e. a compound of formula (II-1), (II-2) or (II-3):

wherein $R^1$ $R^2$ and P are defined as previously described, is reacted with a compound of the following general formula (III):

wherein A is defined as previously described, in an appropriate reaction-inert solvent in the presence of a base, or (b) in order to prepare a compound of formula (I) wherein R is hydrogen, i.e. a compound of the following general formula (I-1), (I-2), or (1-3):

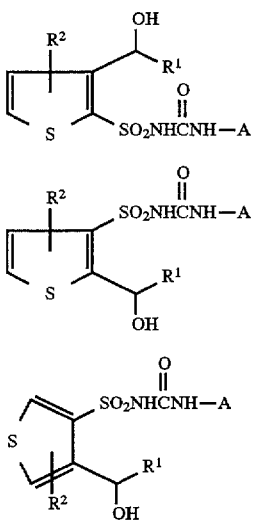

wherein $R^1$, $R^2$ and A are defined as previously described, a compound having the general formula (I-4), (I-5) or (I-6), respectively, obtained in (a) is hydrolyzed with an alkali in the presence of water or an organic solvent.

It is a further object of the present invention to provide an herbicidal composition containing a novel thiophenesulfonylurea derivative as defined above.

BEST MODE FOR CARRYING OUT THE INVENTION

In one aspect, the present invention relates to a novel thiophenesulfonylurea derivative represented by the following general formula (I):

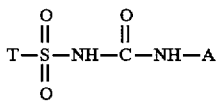

and a salt thereof, in which T and A are as defined above.

In the foregoing definitions for the substituents of the compound of formula (I) according to the present invention, the term "alkyl" defines straight or branched saturated hydrocarbon radicals such as methyl, ethyl, n-propyl, isopropyl or butyl isomers when it is used alone or in the composite form such as "alkylthio" or "haloalkyl"; the term "alkoxy" defines a straight or branched lower alkoxy group having 1 to 6 carbon atoms such as methoxy, ethoxy, n-propoxy, isopropoxy or butoxy isomers; the term "alkenyl" defines a straight or branched alkenyl group having 2 to 7 carbon atoms and a double bond such as vinyl, 1-propenyl, 2-propenyl, or isomers of butenyl, pentenyl, hexenyl or heptenyl; the term "alkynyl" defines a straight or branched alkynyl group having 2 to 7 carbon atoms and a triple bond such as ethynyl, 1-propynyl, 2-propynyl, or isomers of butynyl, pentynyl or hexynyl; and the term "halogen" or "halo" in composite form defines fluorine, chlorine, bromine or iodine.

The preferred herbicidal compounds of formula (I) are those wherein T represents T1, T2 or T3 wherein R represents hydrogen or acetyl, $R^1$ represents methyl or ethyl substituted with halogen and $R^2$ represents hydrogen; and A represents A1 wherein X and Y each independently represents $C_{1-4}$ alkyl, $C_{1-4}$ alkoxy or halogen and Z represents N or CH.

More preferred compounds of formula (I) are those wherein T represents T1 wherein R represents hydrogen or acetyl, $R^1$ represents methyl or ethyl substituted with fluorine or chlorine and $R^2$ represents hydrogen; and A represents A1 wherein X and Y each independently represents methyl, methoxy or chloro and Z represents N or CH.

The most preferred compounds of formula (I) are those wherein T represents T1 wherein R represents hydrogen, $R^1$ represents 1-fluoroethyl and $R^2$ represents hydrogen or chloroethyl; and A represents A1 wherein X and Y each represents methoxy and Z represents CH.

In another aspect, the present invention relates to a process for preparing the compound of formula (I) as defined above.

According to the present invention, the compound of formula (I) wherein R is hydrogen can be prepared by hydrolysing a compound of general formula (I-4), (I-5) or (I-6) with a base in the presence of water or an organic solvent to produce a compound of formula (I-1), (I-2) and (I-3), respectively, as depicted in the following reaction scheme:

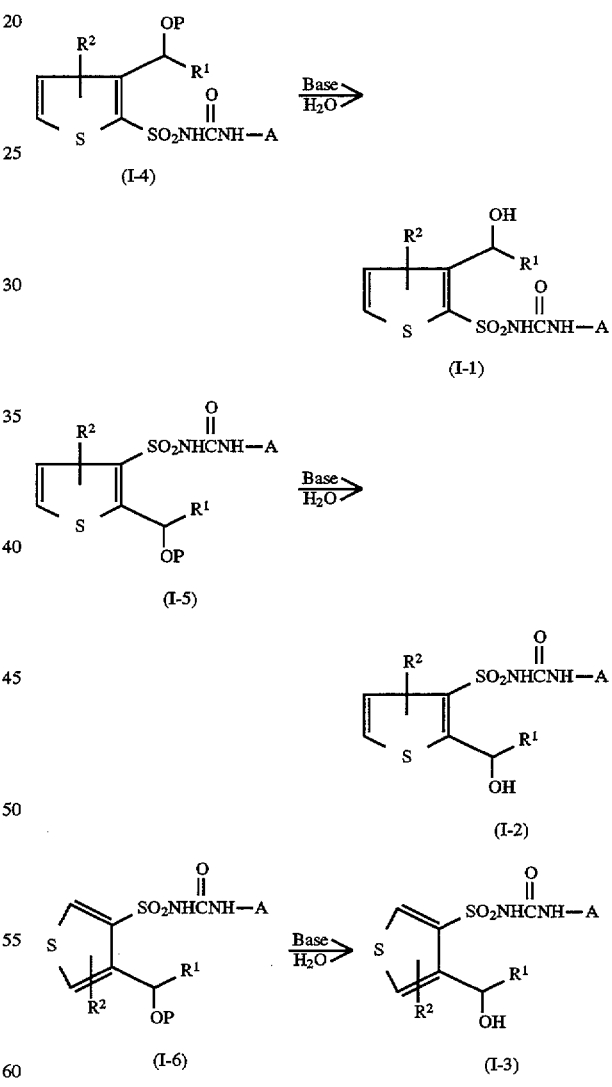

In the above reaction scheme, represents a protecting group which can be easily removed by an acid or an alkali hydrolysis or by any other method, preferably $C_{1-4}$ acyl and most preferably acetyl.

Hydrolysis of the compounds of formulae (I-4) to (I-6) can be conducted by removing a protecting group with a suitable alkali. Suitable alkali which can be preferably used for this purpose includes sodium hydroxide, potassium hydroxide, lithium hydroxide, sodium carbonate, potassium carbonate and the like, with lithium hydroxide being most preferable.

Hydrolysis reaction can be conducted optionally in a reaction-inert solvent, for example, water or organic solvent such as methanol, ethanol, tetrahydrofuran(THF), etc., or the mixture of water and such organic solvent, at the reaction temperature of 0 to 90° C., preferably 0° to 30° C., for 1 to 24 hours, preferably 2 to 4 hours.

The resulting compound of formula (I) wherein R is hydrogen can be easily separated by acidifying with aqueous hydrochloric acid solution. Specifically, the resulting compound can be conveniently obtained by acidifying the reaction mixture with aqueous hydrochloric acid solution, extracting the product with a solvent such as MC(methylene chloride), EA(ethyl acetate), etc. and then concentrating the extract to crystallize the desired product. In addition, when it is desired to obtain the compound of formula (I) wherein R is hydrogen in a highly purified form, the resulting product can be further purified with column chromatography on silica gel.

The compounds of formulae (I-4) to (I-6) used as starting substances in the above reaction scheme 1 can be prepared by reacting a novel compound of the following general formula (II) corresponding to the desired product, i.e. a compound of formula (II-1), (II-2) or (II-3), with a compound of the following general formula (III):

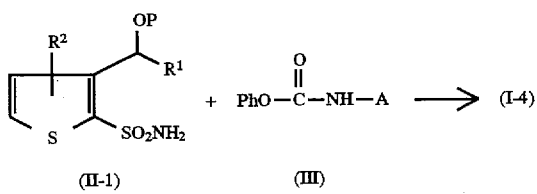

(II-1)      (III)

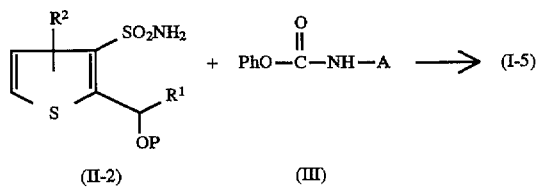

(II-2)      (III)

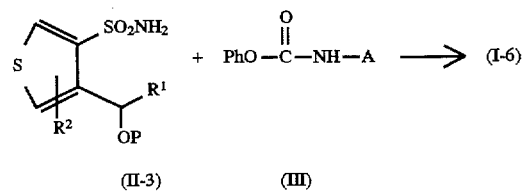

(II-3)      (III)

Wherein $R^1$ and $R^2$ in formulae (II-1) to (II-3) and A in formula (III) are defined as previously described.

The above reaction for elimination of a phenol group can be carried out in an appropriate reaction-inert solvent, for example, an aliphatic or aromatic organic solvent such as dioxane, acetonitrile, THF, acetone, methylene chloride, toluene, butanone, etc. In this reaction, a small quantity of a strong base e.g. Dabco(1,4-diazabicyclo[2,2,2]octane), DHU(1,8-diazabicyclo[5,4,0]undece-7-ene), etc. can also be used as a reaction auxilliary and the reaction temperature is maintained preferably at the range of 20° to 80° C. Alternatively, this reaction can be conducted using an acid as described in U.S. Pat. No. 4,443,245.

The carbamate (III) used in the above reaction can be prepared by reacting diphenylcarbonate or phenylchloroformate with a corresponding amine in the presence of a base like pyridine, according to the following reaction scheme:

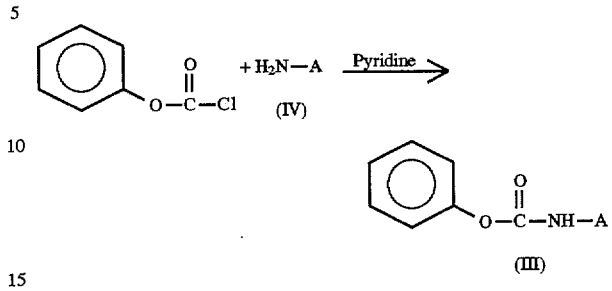

The novel compound of formula (II) including compounds of formulae (II-1), (II-2) and (II-3), can be synthesized according to the following reaction scheme:

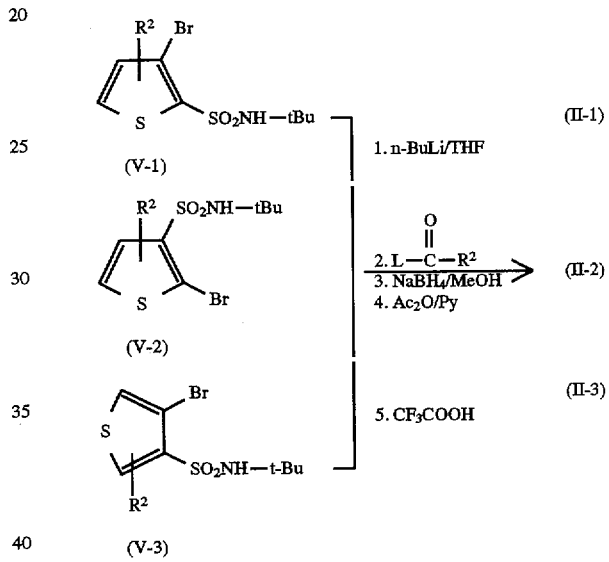

The above reaction will be specifically explained hereinafter. First, a t-butylsulfonamide of formula (V) is treated with 2 equivalences of n-butyllithium in the presence of THF, 1,2-dimethoxyethane or ether, preferably in THF, at −90° to −50° C. for 1 to 24 hours to produce a dili-thio salt to which a compound of formula

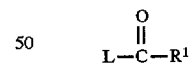

(where in L represents alkoxy, dimethylamide or methyl (methoxy)amide and the like) while maintaining the temperature of −80° to −70° C. to produce a ketone compound. The resulting ketone compound is treated with a reductant like sodium borohydride to produce a hydroxy compound. Such a direct lithiation method of arylsulfonamide can easily be conducted by referring J. G. Lombardino, J. Org. Chem., 36, 1843 (1971) and Stowell, J. G., "Carbanions in Org. Synthesis", John Wiley & Sone New York, 1979, Snieckus, V. Tetrahedron Lett. 26, 1145 (1985) and ibid. 1149 (1985)). In addition, the acylation reaction of a lithiated carbanion and the reduction of ketone compound with lithium aluminumhydride or sodium borohydride to hydroxy compound have been well known in this art.

Then, the hydroxy compound thus produced above is O-acylated with acetic anhydride in the presence of pyridine to obtain a sulfonamide compound. This O-acylation reaction can be facilitated by adding DMAP (4-dimethylaminopyridine) as a catalyst. Finally, the resulting sulfonamide compound is stirred together with an excessive amount of trifluoroacetic acid (about 0.3M) at 0° to 50° C. for 1 to 72 hours to remove N-t-butyl group and to obtain the desired primary sulfonamide compound of formula (II).

This reaction can easily be practiced by a person having ordinary knowledge of organic synthesis by referring J. D. Cart and W. L. Matier, J. Org. Chem., 39, 566 (1974) or by referring J. G. Lombardino, J. Org. Chem., 36, 1843 (1971) when treating with polyphosphoric acid.

The resulting product can be separated by evaporating any volatile substance in the reaction mixture under vacuum and crystallizing the residue with an appropriate solvent such as diethylether, EA, etc. In this case, $R^1$ represents a substituent which is stable against a highly reactive reagent such as n-BuLi.

On the other hand, a heterocyclic amine compound of formula (IV) above can be easily prepared by known processes disclosed in literature or simply modified processes thereof. For example, a method for preparation of amino pyrimidine and triazine substituted with acetal is described in European Patent Application No. 84,224 (published on Jul. 27, 1983) and a report, W. Braker, J. Am. Chem. Soc., 69, 3072 (1947); a method for preparation of amino pyrimidine and triazine substituted with haloalkoxy or haloalkylthio such as $OCHF_2$, $SCHF_2$, $OCH_2OCH_2CF_3$, etc. is disclosed in European Patent No. 72,347 and U.S. Pat. Nos. 4,443,243 and 4,487,915; and a method for preparetion of cyclopropyl pyrimidine and triazine compounds substituted with alkyl, haloalkyl, alkoxy, haloalkoxy, alkylamino, dialkylamino or alkoxyalkyl, etc. is disclosed in European Patent No. 108,708 and U.S. Pat. Nos. 4,515,626 and 4,600,428. In addition, the method for preparation of 5,6-dihydrofuro[2,3-d]pyrimidine-2-amine cyclopenta[d] pyrimidine-2-amine which are compounds of formula (IV) wherein A is A2, and 6,7-dihydro-5H-pyrano[2,3-d] pyrimidine-2-amine which is the compound of for wherein A is A3 is disclosed in European Patent Application No. 15,863; and the method for preparation of [2,3-d]pyrimidine -2-amine compound which is the compound of formula (IV) wherein A is A4 is disclosed in European Patent Application No. 46,677. Further, general methods for preparing amino pyrimidine compounds are fully described in several references (e.g. "The Chemistry of Heterocyclic Compounds", Series. Interscience Publishers, Inc., New York and London; "Pyrimidines", Vol. 16, D. J. Brown Ed; "S-Triazines and Derivatives", Vol. 13, E. M. Smolin and L. Rapaport) and the methods for preparing triazine compounds are also described in another references (e.g. F. C. Schaefer, U.S. Pat. No. 3,154,547 and K. R. Huffman and F. C. Schaefer, J. Org. Chem., 28, 1812 (1963)).

An appropriate salt of the compound of formula (I) prepared according to the present invention above is also useful as a herbicide. Such salt form of the compound (I) can be conveniently prepared by various methods conventionally used in this art. Specifically, the salt form of the compound (I) can be conveniently obtained by treating an acid form of the compound (I) with a sutable base, for example, a solution of alkali metal or alkaline earth metal salt having a strong basic anion such as hydroxide, alkoxide, or carbonate. In addition, a quarternary amine salt of the compound (I) can be prepared by means of an analogous method.

The salt of the compound of formula (I) can also be obtained by exchaning a cation with another one. Generally, this cation exchange reaction can be conducted by contacting an aqueous salt solution of the compound (I) such as aqueous alkali metal salt solution or aqueous quarternary amine salt solution directly with a solution containing any other cation to be exchanged. This exchange reaction can be most efficiently carried out when the salt resulting from the cation exchange reaction is insoluble in water and therefore can be easily separated by filtration.

Alternatively, such ion exchange reaction can be also carried out by subjecting the aqueous solution of the salt of compound (I) to a column filled with a cation exchange resin containing a desired cation to be exchanged. In this method, the desired product is eluted from the column while the original cation of the salt is exchanged with the cation of resin. This method is particularly available when the desired salt is water soluble, that is, it is sodium, potassium, or calcium salt.

Typical examples of the novel compound represented by the general formula (I) which can be prepared according to the process of the present invention are listed in the following Tables 1, 2, and 3.

TABLE 1

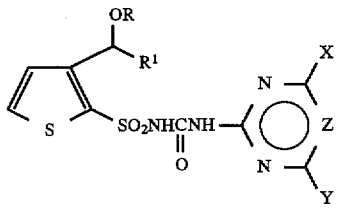

| Comp. No. | R | R¹ | X | Y | Z | m.p. (°C.) | Remarks |
|---|---|---|---|---|---|---|---|
| 1 | O‖CH₃C— | FCH₂— | CH₃O— | CH₃O— | CH | 131–134 | |
| 2 | O‖CH₃C— | FCH₂— | CH₃ | CH₃ | CH | 158–160 | |

TABLE 1-continued

[Structure: thiophene ring with OR and R¹ substituents on a CH group, and SO₂NHC(=O)NH- linked to a pyrazine/pyrimidine ring with X, Y, Z substituents]

| Comp. No. | R | R¹ | X | Y | Z | m.p. (°C.) | Remarks |
|---|---|---|---|---|---|---|---|
| 3 | CH₃C(=O)— | FCH₂— | CH₃ | CH₃O— | N | 154–156 | |
| 4 | H | FCH₂— | CH₃O— | CH₃O— | CH | 135–136 | |
| 5 | H | FCH₂— | CH₃ | CH₃ | CH | 128–129 | |
| 6 | H | FCH₂— | CH₃ | CH₃O— | N | 98–100 | |
| 7 | CH₃C(=O)— | ClCH₂— | CH₃O— | CH₃O— | CH | 150–151 | |
| 8 | CH₃C(=O)— | ClCH₂— | CH₃ | CH₃O— | CH | 182–184 | |
| 9 | CH₃C(=O)— | ClCH₂— | CH₃ | CH₃O— | N | 161–162 | |
| 10 | CH₃C(=O)— | ClCH₂— | CH₃ | CH₃ | CH | 182–184 | |
| 11 | H | ClCH₂— | CH₃O— | CH₃O— | CH | 146–148 | |
| 12 | H | ClCH₂— | CH₃ | CH₃O— | CH | 141–142 | |
| 13 | H | ClCH₂— | CH₃ | CH₃O— | N | 158–159 | |
| 14 | H | ClCH₂— | CH₃ | CH₃ | CH | 143–144 | |
| 15 | CH₃C(=O)— | CH₃CHCl— | CH₃O— | CH₃O— | CH | 162–164 | mixture |
| 16 | CH₃C(=O)— | CH₃CHCl— | CH₃O— | CH₃O— | CH | 167–168 | polar |
| 17 | CH₃C(=O)— | CH₃CHCl— | CH₃O— | CH₃O— | CH | 170–172 | nonpolar |
| 18 | CH₃C(=O)— | CH₃CHCl— | Cl | CH₃O— | CH | 169–170 | mixture |
| 19 | CH₃C(=O)— | CH₃CHCl— | Cl | CH₃O— | CH | 172–174 | polar |
| 20 | CH₃C(=O)— | CH₃CHCl— | Cl | CH₃O— | CH | 177–178 | nonpolar |
| 21 | CH₃C(=O)— | CH₃CHCl— | CH₃ | CH₃ | CH | 176–178 | mixture |
| 22 | CH₃C(=O)— | CH₃CHCl— | CH₃ | CH₃ | CH | 182–183 | polar |
| 23 | CH₃C(=O)— | CH₃CHCl— | CH₃ | CH₃ | CH | 185–186 | nonpolar |

TABLE 1-continued

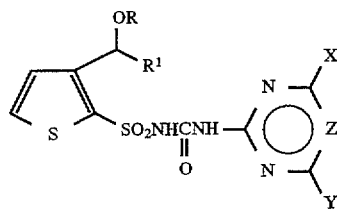

| Comp. No. | R | R¹ | X | Y | Z | m.p. (°C.) | Remarks |
|---|---|---|---|---|---|---|---|
| 24 | CH₃C(=O)— | CH₃CHCl— | CH₃ | CH₃O— | N | 156–157 | mixture |
| 25 | CH₃C(=O)— | CH₃CHCl— | CH₃ | CH₃O— | N | 163–164 | polar |
| 26 | CH₃C(=O)— | CH₃CHCl— | CH₃ | CH₃O— | N | 167–168 | nonpolar |
| 27 | CH₃C(=O)— | CH₃CHCl— | CH₃ | CH₃O— | CH | 168–170 | mixture |
| 28 | CH₃C(=O)— | CH₃CHCl— | CH₃ | CH₃O— | CH | 174–175 | polar |
| 29 | CH₃C(=O)— | CH₃CHCl— | CH₃ | CH₃O— | CH | 179–180 | nonpolar |
| 30 | H | CH₃CHCl— | CH₃O— | CH₃O— | CH | 159–161 | mixture |
| 31 | H | CH₃CHCl— | CH₃O— | CH₃O— | CH | 181–182 | polar |
| 32 | H | CH₃CHCl— | CH₃O— | CH₃O— | CH | 185–186 | nonpolar |
| 33 | H | CH₃CHCl— | Cl | CH₃O— | CH | 169–170 | mixture |
| 34 | H | CH₃CHCl— | Cl | CH₃O— | CH | 174–175 | polar |
| 35 | H | CH₃CHCl— | Cl | CH₃O— | CH | 175–176 | nonpolar |
| 36 | H | CH₃CHCl— | CH₃ | CH₃ | CH | 176–178 | mixture |
| 37 | H | CH₃CHCl— | CH₃ | CH₃ | CH | 182–183 | polar |
| 38 | H | CH₃CHCl— | CH₃ | CH₃ | CH | 187–188 | nonpolar |
| 39 | H | CH₃CHCl— | CH₃ | CH₃O— | N | 166–167 | mixture |
| 40 | H | CH₃CHCl— | CH₃ | CH₃O— | N | 174–175 | polar |
| 41 | H | CH₃CHCl— | CH₃ | CH₃O— | N | 179–180 | nonpolar |
| 42 | H | CH₃CHCl— | CH₃ | CH₃O— | CH | 170–171 | mixture |
| 43 | H | CH₃CHCl— | CH₃ | CH₃O— | CH | 173–174 | polar |
| 44 | H | CH₃CHCl— | CH₃ | CH₃O— | CH | 179–180 | nonpolar |
| 45 | CH₃C(=O)— | CH₃CHF— | CH₃ | CH₃ | CH | 153–154 | mixture |
| 46 | CH₃C(=O)— | CH₃CHF— | CH₃ | CH₃ | CH | 161–162 | polar |
| 47 | CH₃C(=O)— | CH₃CHF— | CH₃ | CH₃ | CH | 168–169 | nonpolar |
| 48 | CH₃C(=O)— | CH₃CHF— | CH₃ | CH₃O— | CH | 151–152 | mixture |
| 49 | CH₃C(=O)— | CH₃CHF— | CH₃ | CH₃O— | CH | 162–163 | polar |
| 50 | CH₃C(=O)— | CH₃CHF— | CH₃ | CH₃O— | CH | 167–168 | nonpolar |
| 51 | CH₃C(=O)— | CH₃CHF— | CH₃O— | CH₃O— | CH | 138–139 | mixture |

TABLE 1-continued

| Comp. No. | R | R¹ | X | Y | Z | m.p. (°C.) | Remarks |
|---|---|---|---|---|---|---|---|
| 52 | CH₃C(=O)— | CH₃CHF— | CH₃O— | CH₃O— | CH | 140–141 | polar |
| 53 | CH₃C(=O)— | CH₃CHF— | CH₃O— | CH₃O— | CH | 145–146 | nonpolar |
| 54 | CH₃C(=O)— | CH₃CHF— | CH₃O— | Cl | CH | 165–166 | mixture |
| 55 | CH₃C(=O)— | CH₃CHF— | CH₃O— | Cl | CH | 167–168 | polar |
| 56 | CH₃C(=O)— | CH₃CHF— | CH₃O— | Cl | CH | 171–172 | nonpolar |
| 57 | CH₃C(=O)— | CH₃CHF— | CH₃O— | CH₃ | N | 154–156 | mixture |
| 58 | CH₃C(=O)— | CH₃CHF— | CH₃O— | CH₃ | N | 169–170 | polar |
| 59 | CH₃C(=O)— | CH₃CHF— | CH₃O— | CH₃ | N | 177–178 | nonpolar |
| 60 | H | CH₃CHF— | CH₃ | CH₃ | CH | 152–153 | mixture |
| 61 | H | CH₃CHF— | CH₃ | CH₃ | CH | 157–158 | polar |
| 62 | H | CH₃CHF— | CH₃ | CH₃ | CH | 167–168 | nonpolar |
| 63 | H | CH₃CHF— | CH₃ | CH₃O— | CH | 140–142 | mixture |
| 64 | H | CH₃CHF— | CH₃ | CH₃O— | CH | 161–162 | polar |
| 65 | H | CH₃CHF— | CH₃ | CH₃O— | CH | 170–171 | nonpolar |
| 66 | H | CH₃CHF— | CH₃O— | CH₃O— | CH | 152–154 | mixture |
| 67 | H | CH₃CHF— | CH₃O— | CH₃O— | CH | 160–161 | polar |
| 68 | H | CH₃CHF— | CH₃O— | CH₃O— | CH | 167–168 | nonpolar |
| 69 | H | CH₃CHF— | CH₃O— | Cl | CH | 157–158 | mixture |
| 70 | H | CH₃CHF— | CH₃O— | Cl | CH | 161–162 | polar |
| 71 | H | CH₃CHF— | CH₃O— | Cl | CH | 171–172 | nonpolar |
| 72 | H | CH₃CHF— | CH₃O— | CH₃ | N | 141–142 | mixture |
| 73 | H | CH₃CHF— | CH₃O— | CH₃ | N | 167–168 | polar |
| 74 | H | CH₃CHF— | CH₃O— | CH₃ | N | 163–165 | nonpolar |

TABLE 2

[Structure: thiophene ring with SO₂NHC(=O)NH- linked to a triazine/pyrimidine ring bearing X and Y substituents, and with CHR¹(OR) substituent on thiophene]

| Comp. No. | R | R¹ | X | Y | Z | m.p. (°C.) | Remarks |
|---|---|---|---|---|---|---|---|
| 75 | CH₃C(O)— | FCH₂— | CH₃ | CH₃ | CH | 144–146 | |
| 76 | CH₃C(O)— | FCH₂— | CH₃ | CH₃O— | CH | 139–141 | |
| 77 | CH₃C(O)— | FCH₂— | CH₃O— | CH₃O— | CH | 130–132 | |
| 78 | CH₃C(O)— | FCH₂— | CH₃O— | Cl | CH | 138–139 | |
| 79 | CH₃C(O)— | FCH₂— | CH₃O— | CH₃ | N | 135–136 | |
| 80 | CH₃C(O)— | FCH₂— | CH₃O— | CH₃O— | N | 129–131 | |
| 81 | H | FCH₂— | CH₃ | CH₃ | CH | 152–154 | |
| 82 | H | FCH₂— | CH₃— | CH₃O— | CH | 121–122 | |
| 83 | H | FCH₂— | CH₃O— | CH₃O— | CH | 132–134 | |
| 84 | H | FCH₂— | CH₃O— | Cl | CH | 139–140 | |
| 85 | H | FCH₂— | CH₃O— | CH₃ | N | 141–142 | |
| 86 | H | FCH₂— | CH₃O— | CH₃O— | N | 135–137 | |
| 87 | CH₃C(O)— | CH₃CHF— | CH₃O— | CH₃ | CH | 155–157 | mixture |
| 88 | CH₃C(O)— | CH₃CHF— | CH₃O— | CH₃ | CH | 163–165 | polar |
| 89 | CH₃C(O)— | CH₃CHF— | CH₃O— | CH₃ | CH | 172–173 | nonpolar |
| 90 | CH₃C(O)— | CH₃CHF— | CH₃O— | CH₃O— | CH | 135–136 | mixture |
| 91 | CH₃C(O)— | CH₃CHF— | CH₃O— | CH₃O— | CH | 141–142 | polar |
| 92 | CH₃C(O)— | CH₃CHF— | CH₃O— | CH₃O— | CH | 168–170 | nonpolar |
| 93 | CH₃C(O)— | CH₃CHF— | CH₃O— | CH₃ | N | 121–124 | mixture |
| 94 | CH₃C(O)— | CH₃CHF— | CH₃O— | CH₃ | N | 131–132 | polar |
| 95 | CH₃C(O)— | CH₃CHF— | CH₃O— | CH₃ | N | 142–143 | nonpolar |

TABLE 3

[Structure: thiophene with OR and R¹ substituent on CH, SO₂NHCNH linked to pyrimidine/triazine ring with X, Y, Z]

| Comp. No | R | R¹ | X | Y | Z | m.p.(°C.) | Remarks |
|---|---|---|---|---|---|---|---|
| 96 | CH₃C(O)— | CH₃CHF— | CH₃ | CH₃O— | CH | 158–159 | polar |
| 97 | CH₃C(O)— | CH₃CHF— | CH₃ | CH₃O— | CH | 149–150 | nonpolar |
| 98 | CH₃C(O)— | CH₃CHF— | CH₃O— | CH₃O— | CH | 138–139 | polar |
| 99 | CH₃C(O)— | CH₃CHF— | CH₃O— | CH₃O— | CH | 131–134 | nonpolar |
| 100 | CH₃C(O)— | CH₃CHF— | CH₃ | CH₃O— | N | 177–178 | polar |
| 101 | CH₃C(O)— | CH₃CHF— | CH₃ | CH₃O— | N | | nonpolar |
| 102 | H | CH₃CHF— | CH₃ | CH₃ | CH | 178–179 | polar |
| 103 | H | CH₃CHF— | CH₃ | CH₃ | CH | 161–162 | nonpolar |
| 104 | H | CH₃CHF— | CH₃ | CH₃O— | CH | 150–151 | polar |
| 105 | H | CH₃CHF— | CH₃ | CH₃O— | CH | 143–144 | nonpolar |
| 106 | H | CH₃CHF— | CH₃O— | CH₃O— | CH | 183–184 | polar |
| 107 | H | CH₃CHF— | CH₃O— | CH₃O— | CH | 171–172 | nonpolar |
| 108 | H | CH₃CHF— | CH₃ | CH₃O— | N | 90–91 | polar |
| 109 | H | CH₃CHF— | CH₃ | CH₃O— | N | 99–100 | nonpolar |
| 110 | H | CH₂F | CH₃ | Cl | CH | | |
| 111 | H | CH₂F | CH₃ | CH₃ | CH | 92–95 | |
| 112 | H | CH₂F | CH₃ | OCH₃ | CH | 135–138 | |
| 113 | H | CH₂F | OCH₃ | OCH₃ | CH | 139–141 | |
| 114 | H | CH₂F | OCH₃ | CH₃ | N | 102–105 | |
| 115 | CH₃C(O)— | CH₂F | CH₃ | Cl | CH | | |
| 116 | CH₃C(O)— | CH₂F | CH₃ | CH₃ | CH | 178–179 | |
| 117 | CH₃C(O)— | CH₂F | CH₃ | OCH₃ | CH | 161–162 | |
| 118 | CH₃C(O)— | CH₂F | OCH₃ | OCH₃ | CH | 150–151 | |
| 119 | CH₃C(O)— | CH₂F | OCH₃ | OCH₃ | N | 140–143 | |
| 120 | CH₃C(O)— | CH₃CHF | CH₃ | OCH₃ | CH | 157–158 | mixture |
| 123 | CH₃C(O)— | CH₃CHF | OCH₃ | OCH₃ | CH | 138–139 | mixture |

Among the compounds of formula (I) as exemplified in the tables above, for example, a compound wherein R¹ is 1-fluoroethyl can be present in different stereochemical isomeric forms because it has at least 2 asymmetric carbon atoms in the substituent located at 3-position of the thienyl group. Therefore, these isomeric forms of the compound (I) are also encompassed within the scope of the present invention. The stereoisomeric racemates having polar and non-polar forms can be separated by known methods, e.g. column chromatography, thin layer chromatography, high performance liquid chromatography, into pure stereoisomeric forms. In the present invention thin layer chromatography or column chromatography on silica gel is selected. Since these stereochemical configurations are early determined on the intermediate of formulae (I-4) to (I-6) and formula (II), the corresponding isomeric form of formula (I) can be obtained by separating such intermediates into the desired stereochemical isomers which are then treated according to the process of the present invention.

the compound (I) of the present invention exhibits markedly high herbicidal activities either before or after emergence of weeds to be controlled. Accordingly, the use of the compound of formula (I) as a herbicide for controlling weeds is also one object of the present invention.

Weeds herein, in the broadest sense, can be understood all plants which grow in locations where they are undesired.

3-(i-acetoxy-chloroethyl)-N-[(4,6-dimethoxypyrimidin-2-yl) aminocarbonyl]-2-thiophenesulfonamide among the compound of formula (I) according to the present invention has an excellent herbicidal activity, particularly against Flatsedge and Arrowhead, as herbicide for water conduit.

The amounts of the active compound (I) according to the present invention to be used can be determined depending on the kind of crops to be protected or weeds to be controlled, and climate, weather, formulation, method of application, soil, and size of weeds. In general, the active compound is used in an amount of 0.01 to 10 kg per hectare, but can be used in an amount lower than the above defined amount when the soil to be treated has little organic matter or is a sandy soil.

For combating weeds, the active compound according to the present invention can be used alone or in a combination with known other herbicides. Suitable herbicide which can be used in the combination with the compound (I) according to the present invention can be exemplified as follows:

| Common Name | |
|---|---|
| acetochlor | acifluorfen |
| AC252, 214 | AC263, 499 |
| acrolein | alachlor |
| ametryn | amitrole |
| AMS | asulam |
| ASSURE | atrazine |
| BAS-514 | barban |
| benefin | bensulfuron methyl |
| bensulide | bentazon |
| benzolfluor | benzoylprop |
| bifenox | bromacil |
| bromoxynil | butachlor |
| buthidazole | butralin |
| buthilate | cacodylic acid |
| CDAA | CDEC |
| CGA 82725 | CH-83 |
| chloramben | chlorbromuron |
| chlorimuron ethyl | chloroxuron |
| chlorporpham | chlorsulfuron |
| chlortoluron | cinmethylin |
| clethodim | clomazone |
| cloproxydim | clopyralid |
| CMA | cyanazine |
| cycloate | cycluron |
| cyperquat | cyprazine |
| cyprazole | cypromid |

-continued

| Common Name | |
|---|---|
| dalapon | dazomet |
| DCPA | desmediphan |
| desmetryn | diallate |
| dicamba | dichlorbenil |
| dichlorprop | dichlorfop |
| diethatyl | difenzoquar |
| diphenmid | dipropetryn |
| diquat | diuron |
| DNOC | DOWCO 453 ME |
| DPX-M6316 | DSMA |
| endothall | EPTC |
| enthalfluralin | ethofumesate |
| EXPRESS | fenac |
| fenoxapropethyl | fenuron |
| fenuron TCA | flamprop |
| fluazifop | fluazifopbutyl |
| fluometuron | fluorochloridone |
| fluorodifen | fluoroglycofen |
| fluridone | fomesafen |
| fosamine | glyphosate |
| haloxyfop | harmoney |
| hexaflurate | hexazinone |
| HW-52 | imazamethabez |
| imazapyr | imazaquin |
| imazthapyr | ioxynil |
| isopropalin | isoproturon |
| isouron | isoxaben |
| karbutilate | lactofen |
| lenacil | linuron |
| MAA | MAMA |
| MCPA | MCPB |
| mecoprop | mefluidide |
| methalpropalin | methabenzthiazuron |
| metham | methazole |
| methoxuron | metolachlor |
| metribuzin | metsulfuron methyl |
| MH | milinate |
| monolinuron | monuron |
| monuron TCA | MSMA |
| My-93 | naproparmide |
| naproanilide | naptalam |
| neburon | nitralin |
| nitrofen | nitrofluorten |
| norea | norfrurazon |
| NTN-801 | oryzalin |
| oxadiazon | oxyfluorfen |
| paraquat | pebulate |
| pendimethalin | perfluidone |
| phenmedipham | picloram |
| PPG-1013 | pretilachlor |
| procyazine | profluralin |
| prometon | prometryn |
| pronamide | propachlor |
| propanil | propazine |
| propham | prosulfalin |
| prynachlor | pyrazon |
| pyrazolate | quizalotop |
| quizalotop ethyl | SC-2957 |
| secbumeton | sethoxydim |
| siduron | simazine |
| SL-49 | sulfometuron methyl |
| TCA | tebuthiuron |
| terbacil | teruchlor |
| terbuthyiazine | terbutol |
| terbutryn | thiameruron methyl |
| thiobencarb | triallate |
| riclopyr | tridiphane |
| trifluralin | trimeturon |
| 2,4-D | 2,4-DB |
| vernolate | X-52 |
| xylachlor | Saturn |
| KH-218 | NSK-850 |
| Pyrazoxyfen | Dimension |
| CH-900 | Mefenacet |
| TSH-888 | Dymron |
| Dimepiperate | Isoxapyrifos |
| Phenobenzuron | JC-940 |
| Esprocab | Methylbencab |

-continued

| Common Name | |
|---|---|
| Phenopylate | Benfuresate |
| S-275 | Quinclorac |
| Londax | NC-311 |
| TH-913 | HW-52 |
| DEH-112 | SKH-301 |
| Bromobutide | BAS517H |
| RE45601 | RE36299 |
| RO173664 | HOE075632 |
| ICIA6051 | DPXA7881 |
| MW801 | CGA136872 |
| DPXV9360 | DPXE9636 |
| SL950 | ICIA02957 |
| CGAI42464 | MY15 |
| MON7200 | WL95481 |
| DPXY6202 | MON15100 |
| SL160 | ICIA0224 |
| LS83556 | BAS518H |
| CGA131036 | DPXL5300 |
| HOE70542 | ICIA0604 |

The preparation and use of the active compound according to the present invention are more specifically explained by the following examples. However, it should be understood that they are provided only as representative embodiment of the present invention and are not intended to limit the scope of the present invention thereto.

EXAMPLE 1

Synthesis of N-t-butyl-3-(fluoroacetyl)-2-thiophenesulfonamide 2.98 g (0.0mole) of N-t-butyl-3-bromo-2-thiophenesulfonamide was dissolved in 50mi of dry tetrahydrofuran and the mixture was cooled to −78° C. under nitrogen gas. To the reaction solution was slowly added dropwise 8.4 ml of n-butyl lithium (2.5N) and then the temperature of the mixture was raised slowly to −20° C. and again cooled to −78° C. 1.2 g (0.011 mole) of ethyl fluoroacetate was added slowly to the reaction mixture. The temperature of the mixture was raised again slowly to −20° C. and then the mixture was stirred for 10 minutes. To the reaction mixture was added 100 ml of 5% aqueous ammonium chloride solution, and then added 100 ml of ethylacetate to separate the organic layer. The extracted organic layer was dried over anhydrous magnesium sulfate and concentrated. The residue was subjeced to column chromatography on silica gel to obtain 2.0 g (Yield: 72%) of the pure title compound as a liquid.

$^1$H NMR(CDCl$_3$, δ): 1.25(s, 9H), 5.4(d, 2H), 6.1(s, 1H), 7.3–7.6 (m, 2H)

EXAMPLE 2

Synthesis of N-t-butyl-3-(1-acetoxy-2-fluoroethyl)-2-thiophenesulfonamide 1.4 g (0.005 mole) of N-t-butyl-3-(fluoroacetyl)-2-thiophenesulfonamide synthesized in Example 1 was dissolved in 100 ml of methanol and then 190 mg (0.005 mole) of sodium borohydride (NaBH$_4$) was added slowly thereto. The mixture was stirred at 40° C. for 30 minutes and then concentrated under reduced pressure. The residue was dissolved in 30 ml of methylene chloride and the resulting solution was washed with 5% aqueous hydrochloric acid solution. To the solution were added acetic anhydride, pyridine and N,N-dimethyl amidepyridine, and the mixture was stirred at normal temperature for 24 hours and then washed with 5% aqueous hydrochloric acid solution. The organic layer was separated, dried over anhydrous magnesium sulfate and filtered. The filtrate Was concentrated and the residue was subjected to column chromatography on silica gel to obtain 1.4 g (Yield: 85% of the title compound.

$^1$H NMR(CDCl$_3$, δ): 1.23(s, 9H), 2.13(s, 3H), 4.65(dd, 2H), 5.7(s, 1H), 6.55 (dt, 1H), 7.2 (dd, 1H), 7.5(d, 1H)

EXAMPLE 3

Synthesis of 3-(1-acetoxy-2-fluoroethyl)-2-thiophenesulfonamide 1.4 g (0.0043 mole) of N-t-butyl-3-(1-aceoxy-2-fluoroethyl) -2-thiophenesulfonamide synthesized in Example 2 dissolved in 5 ml of trifluoroacetic acid. The reaction solution was stirred at normal temperature for 12 hours and then concentrated under reduced pressure. The residue was dissolved in methylene chloride and washed with aqueous sodium bicarbonate solution. The organic layer was separated, dried over anhydrous magnesium sulfate and then filtered. The filtrate was concentrated. The residue was recrystallized to obtain 750 mg (Yield: 74%) of the pure title compound as a white solid.

m.p. : 94°–96° C. $^1$H NMR(CDCl$_3$, δ): 2.13(s, 3H), 4.55(dd, 2H), 5.7(s, 2H), 6.55(dt, 1H), 7.2(dd, 1H), 7.53(d, 1H)

EXAMPLE 4

Synthesis of N-[(4,6-dimethoxypyrimidin-2-yl)-aminocarbonyl]-3-(1-acetoxy-2-fluoroethyl)-2-thiophenesulfonamide (Compound No. 1)

667 mg (0.0025 mole) of 3-(1-acetoxy-2-fluoroethyl)-2-thiophenesulfonamide synthesized in Example 3 and 687 mg (0.0025 mole) of N-(4,6-dimethoxy-2-pyrimidinyl)-O-phenylcarbamate were dissolved in 10 ml of dry acetonitrile. To the reaction solution was added 400 mg of DBU, and the mixture was stirred at normal temperature for 4 hours and then concentrated. The residue was dissolved in 90 ml of methylene chloride, and the resulting solution as washed with 5% aqueous HCl solution. The organic layer was separated, dried and then concentrated. The residue was recrystallized to obtain 835 mg (Yield: 78%) of the pure title compound as a while solid.

m.p. : 131°–134° C. $^1$H NmR(CDCl$_3$, δ): 2.13(s, 3H), 4.01(s, 6H), 4.48–4.97(m, 2H), 5.85(s, 1H), 6.61–6.78(m, 1H), 7.24 (br, 1H), 7.2–7.75(m, 2H), 13.1(s, 1H)

EXAMPLE 5

Synthesis of N-[(4,6-dimethoxypyrimidin-2-yl)-aminocarbonyl]-3-(1-hydroxy-2-fluoroethyl)-2-thiophenesulfonamide (Compound No. 4)

650 mg (0.0015 mole) of N-[(4,6-dimethoxypyrimidin-2-yl)aminocarbonyl]-3-(1-acetoxy-2-fluoroethyl)-2-thiophenesulfonamide synthesized in Example 4 was dissolved in 5 ml of aqueous sodium hydroxide solution and then stirred at normal temperature for one hour. The reaction mixture was adjusted to pH4 by adding 5% aqueous HCl solution and then extracted with methylene chloride. The extract was concentrated to obtain 540 mg (Yield: 92%) of the pure title compound.

m.p. : 135°–136° C. $^1$H NMR(CDCl$_3$, δ): 4.01(s, 6H), 4.41–4.88(m, 2H), 5.85 (s, 1H), 5.91–6.08(m, 1H), 7.55(s, 1H), 7.3–7.7(m, 2H), 13.0(s, 1H)

EXAMPLE 6

Synthesis of N-t-butyl-3-chloroacetyl-2-thiophenesulfonamide 2.98 g (0.0! mole) of N-t-butyl-3-bromo-2-thiophenesulfonamide was dissolved in 50 ml of dry tetrahydrofura mixture was cooled to −78° C. under nitrogen gas. To the reaction solution was slowly added dropwise 8.4 ml of n-butyl lithium(2.5N) and then the temperature of the mixture was raised slowly to −20° C. and again cooled to −78° C. 1.4 g (0.012 mole) of ethyl chloroacetates was added slowly to the mixture. The temperature of the reaction mixture was raised slowly to −20° C. again and then the mixture was stirred for 10 minutes. To the mixture was added 100 ml of aqueous ammonium chloride solution and then added 100 ml of ethyl acetate to separate the organic layer. The extracted organic layer was dried over anhydrous magnesium sulfate and then concentrated. The residue was subjected to column chromatography on silica gel to obtain 1.9 g (Yield: 69%) of the pure title compound as a liquid.

$^1$H NMR(CDCl$_3$, δ): 1.25(s, 9H), 4.7(s, 2H), 6.7(s, 1H), 7.52 (d, 1H), 7.57 (d, 1H)

EXAMPLE 7

Synthesis of N-t-butyl-3-(1-acetoxy-2-chloroethyl)-2-thiophenesulfonamide 1.5 g (0.005 mole) of N-t-butyl-3-(chloroacetyl)-2-thiophenesulfonamide synthesized in Example 6 was dissolved in the combined solution of 1 ml of acetic acid and 10 ml of tetrahydrofuran and then 0.31 g (0.005 mole) of sodium cyanoborohydride was added slowly thereto. The reaction solution was stirred at normal temperature for 30 minutes and then subjected to a vacuum evaporator to remove the solvent. To the residue was added 10 ml of water and then the resulting solution was extracted with methylene chloride. The extract was dried over anhydrous magnesium sulfate and filtered. To the filtrate were added acetic anhydride, pyridine and N,N-dimethylaminopyridine and the mixture was stirred at normal temperature for 24 hours and then washed with 5% aqueous hydrochloric acid solution. The organic layer was separated, dried over anhydrous magnesium sulfate and filtered. The filtrate was concentrated and the residue was subjected to column chromatography on silica gel to obtain 5 g (Yield: 84%) of the title compound. $^1$H NMR(CDCl$_3$, δ): 1.3(s, 9H), 2.15(s, 3H), 3.57–3.9(m, 2H), 5.23(s, 1H), 6.5(m, 1H), 7.13(d, 1H), 7.5 (d, 1H)

EXAMPLE 8

Synthesis of 3-(1-acetoxy-2-chloroethyl)-2-thiophenesulfonamide 1.5 g (0.0044 mole) of N-t-butyl-3-(1-acetoxy-2-chloroethyl)-2-thiophenesulfonamide synthesized in Example 7 was dissolved in 5 ml of trifluoroacetic acid. The reaction solution was stirred at normal temperature for 12 hours and then concentrated under reduced pressure. The residue was dissolved in methylene chloride and the solution was washed with aqueous sodium bicarbanate solution. The organic layer was separated, dried over anhydrous magnesium sulfate and filtered. The filtrate was then concentrated. The residue was subjected to column chromatograpy on silica gel to obtain 760 mg (Yield: 72%) of the pure title compound.

m.p. : 90°–91° C. $^1$H NMR(CDCl$_3$, δ): 2.1(s, 3H), 3.75–3.85(m, 2H), 5.55(s, 1H), 6.5(m, 1H), 7.5(d, 1H), 7.52(d, 1H)

EXAMPLE 9

Synthesis of N-[(4,6-dimethoxypyrimidin-2-yl)-aminocarbonyl]-3-(1-acetoxy-2-chloroethyl)-2-thiophenesulfonamide (Compound No. 7)

709 mg (0.0025 mole) of 3-(1-acetoxy-2-chloroethyl)-2-thiophenesulfonamide synthesized in Example 8 and 687 mg (0.0025 mole) of N-(4,6-dimethoxy-2-pyrimidinyl)-O-phenylcarbamate were treated according to the same procedure as Example 4 to obtain 750 mg (Yield: 70%) of the pure title compound.

m.p.: 150°–151° C. $^1$H NMR(CDCl$_3$, δ): 2.02(s, 3H), 3.81–3.98(m, 2H), 4.0(s, 6H), 5.8(s, 1H), 6.61(m, 1H), 7.21–7.67 (m, 2H), 7.3(s, 1H), 13.18(s, 1H)

EXAMPLE 10

Synthesis of N-t-butyl-2-(fluoroacetyl)-3-thiophenesulfonamide 1.87 g (0.01 mole) of N-t-butyl-3-thiophenesulfonamide was treated according to the same procedure as Example 1 to obtain 2.1 g (Yield: 76%) of the pure title compound as a liquid.

$^1$H NMR(CDCl$_3$, δ): 1.25(s, 9H), 5.4(d, 2H), 6.1(s, 1H), 7.3–7.6 (m, 2H)

EXAMPLE 11

Synthesis of N-t-butyl-2(1-acetoxy-2-fluoroethyl)-3-thiophenesulfonamide 1.4 g (0.005 mole) of N-t-butyl-2-(fluoroacetyl)-3-thiophenesulfonamide synthesized in Example 10 was treated according to the same procedure as Example 2 to obtain 1.5 g (Yield: 91%) of the title compound.

$^1$H NMR(CDCl$_3$, δ): 1.23(s, 9H), 2.13(s, 3H), 4.45–4.88 (m, 2H), 5.2 (s, 1H), 6.82 (dt, 1H), 7.25–7.4 (m, 2H)

EXAMPLE 12

Synthesis of 2-(1-acetoxy-2-fluoroethyl)-3-thiophenesulfonamide 1.4 g (0.0043 mole) of N-t-butyl-2-(1-acetoxy-2-fluoroethyl)-3-thiophenesulfonamide synthesized in Example 11 was treated according to the same procedure as Example 3 to obtain 750 mg (Yield.: 74%) of the pure title compound as a white solid.

m.p.: 97°–98° C. $^1$H NMR(CDCl$_3$, δ): 2.13(s, 3H), 4.67 (dd, 2H), 5.58(s, 2H), 6.52(dt, 1H), 7.2(dd, 1H),7.55(d, 1H)

EXAMPLE 13

Synthesis of N-[(4,6-dimethoxypyrimidin-2-yl)-aminocarbonyl]-2-(1-acetoxy-2-fluoroethyl)-3-thiophenesulfonamide (Compound No. 77)

667 mg (0.0025 mole) of 2-(1-acetoxy-2-fluoroethyl)-3-thiophenesulfonamide synthesized in Example 12 and 687 mg (0.0025 mole) of N-(4,6-dimethoxy-2-pyrimidinyl)-O-phenyl-carbamate were treated according to the same procedure as Example 4 to obtain 780 mg (Yield: 73%) of the pure title compound as a white solid.

m.p. : 130°–132° C.

$^1$H NMR(CDCl$_3$, δ): 2.19(s, 3H), 4.01(s, 6H), 4.6–5.0(m, 2H), 5.81(s, 1H), 6.98–7.0(m,1H), 7.3(s, 1H), 7.38–7.6(d, 2H), 12.82(s, 1H)

EXAMPLE 14

Synthesis of N-[(4r6-dimethoxypyrimidin-2-yl)-aminocarbonyl]-2-(1-hydroxy-2-fluoroethyl)-3-thiophenesulfonamide (Compound No. 83)

650 mg (0.0015 mole) of N-[(4,6-dimethoxypyrimidin-2-yl)-aminocarbonyl]-2-(1-acetoxy-2-fluoroethyl)-3-thiophenesulfonamide synthesized in Example 13 was treated a the same procedure as Example 5 to obtain 528 mg (Yield: 90%) of the pure title compound.

m.p. : 132°–134° C.

$^1$H NHR(CDCl$_3$, δ): 4.0(s, 6H), 4.6–5.0(m, 2H), 5.81(s, 1H), 5.91–6.08(m, 1H), 7.55(s, 1H), 7.3–7.7 (m, 2H), 13.0(s, 1H)

EXAMPLE 15

Synthesis of N-t-butyl-4-(2-fluoropropionyl)-3-thiophenesulfonamide 2.98 g (0.01 mole) of N-t-butyl-4-bromo-3-thiophene sulfonamide was dissolved in 50 ml of dry tetrahydrofuran and the mixture was cooled to –78° C. under nitrogen gas. To the reaction solution was slowly added dropwise 8.4 ml of n-bury lithium (2.5N) and then the temperature of the mixture was raised slowly to –20° C. and again cooled to –78° C. 1.32 g (0.011 mole) of ethyl fluoropropionyl was added slowly to the reaction mixture. The temperature of the mixture was raised slowly to –20° C. again and then the mixture was stirred for 10 minutes. To the mixture was added 100 ml of 5% aqueous ammonium chloride solution and then added 100 ml of ethylacetate to separate the organic layer. The extracted organic layer was dried over anhydrous magnesium sulfate and concentrated. The residue was subjected to column chromatography on silica gel to obtain 1.77 g (Yield: 68%) of the pure title compound as a liquid.

$^1$H NMR(CDCl$_3$, δ): 1.23(s, 9H), 1.65(dd, 3H), 5.45(dt, 2H), 6.18(s, 1H), 7.65–7.75(m, 2H)

EXAMPLE 16

Synthesis of polor and nonpolar N-t-butyl-4-(1-acetoxy-2-fluropropyl)-3-thiophenesulfonamide 2.6 g (0.01 mole) of N-t-butyl-4-(fluropropionyl)-3-thiophenesulfonamide was dissolved in 100 ml of methanol and then 380 mg (0.01 mole) of sodium borohydride was added slowly thereto. The reaction solution was stirred at 40° C. for 30 minutes and then concentrated under reduced pressure. The residue was dissolved in 30 ml of methylene chloride and washed with 5% aqueous hydrochloric acid solution. To the solution were added acetic anhydride, pyridine and N,N-dimethylamido pyridine and the mixture was stirred at normal temperature for 24 hours and then washed with 5% aqueous hydrochloric acid solution. The organic layer was separated, dried over anhydrous magnesium sulfate and filtered. The filtrate was concentrated and the residue was identified as a mixture of erythro and threo diastereomers by thin layer chromatography. The isomers were separated by column chromatography on silica gel to obtain the polar and nonpolar title compound.

polar compound: 1.2 g (Yield: 86%) $^1$H NMR(CDCl$_3$, δ); 1.25(s, 9H), 1.31(dt, 3H), 2.1(s, 3H), 4.8(s, 1H), 4.8–5.2(m, 1H), 6.25(dd, 1H), 7.2–7.4(m, 2H)

nonpolar compound: 1.1 g (Yield: 78%) $^1$H NMR(CDCl$_3$, δ); 1.25(s, 9H), 1.32(dt, 3H), 2.1(s, 3H), 4.8(s, 1H), 4.8–5.3 (m, $^1$H), 6.15(dd, 1H), 7.2–7.4(m, 2H)

EXAMPLE 17

Synthesis of 4-(1-acetoxy-2-fluoropropyl)-3-thiophenesulfonamide (polar)

1.4 g (0.0043 mole) of N-t-butyl-4-(1-acetoxy-2-fluoropropyl)-3-thiophenesulfonamide (polar) synthesized in Example 16 was treated according to the same procedure as Example 3 to obtain 750 mg (Yield: 74%) of the pure title compound as a white solid.

m.p.: 92°–94° C. $^1$ H NMR(CDCl$_3$, δ): 1.25(dt, 3H), 2.1(s, 3H), 4.85–5.25 (m, 1H), 5.55(s, 2H), 6.35(dd, 1H), 7.1–7.2(m, 2H)

EXAMPLE 18

Synthesis of 4-(1-acetoxy-2-fluoropropyl)-3-thiomphenesulfonamide(nonpolar)

1.4 g (0.0043 mole) of N-t-butyl-4-(1-acetoxy-2-fluoropropyl) propyl)-3-thiophenesulfonamide (nonpolar) synthesized in Example 16 was treated according to the same procedure as Example 3 to obtain 750 mg (Yield: 74%) of the pure title compound as a which solid.

m.p. : 91°–93° C.

$^1$H NMR(CDCl$_3$, δ): 1.32(dt, 3H), 2.1(s, 3H), 4.6–5.1(m, 1H), 5.65(s, 2H), 6.28(dd, 1H), 7.1–7.2(m, 2H)

EXAMPLE 19

Synthesis of N-[(4,6-dimethoxypyrimidin-2-yl) aminocarbonyl]-4-(1-acetoxy-2-fluoropropyl)-3-thiophenesulfonamide (molar) (Compound No. 98)

670 mg (0.0025 mole) of 4-(1-acetoxy-2-fluoropropyl)-3-thiophenesulfonamide (polar) synthesized in Example 17 and 687 mg (0.0025 mole) of N-(4,6-dimethoxy-2-pyrimidinyl)-O-phenylcarbamate were treated according to the same procedure as Example 4 to obtain 853 mg (Yield: 78%) of the pure title compound as a white solid.

m.p. : 138°–139° C.

$^1$H NMR(CDCl$_3$, δ): 1.5(m, 3H), 4.01(s, 6H), 5.0(m, 1H), 6.0(dd, 1H), 6.78(s, 1H), 7.3–7.4(m, 2H), 9.2(s, 1H), 13.1(s, 1H)

EXAMPLE 20

Synthesis of N-[(4,6-dimethoxypyrimidin-2-yl) aminocarbonyl-4-(1-acetoxy-2-fluoropropyl)-3-thiophenesulfonamide(nonpolar)(Compound No. 99.)

670 mg (0.0025 mole) of 4-(1-acetoxy-2-fluoropropyl)-3-thiophenesulfonamide (nonpolar) synthesized in Example 18 and 687 mg (0.0025 mole) of N-(4,6-dimethoxypyrimidin-2-pyrimidinyl)-O-phenylcarbamate were treated according to the same procedure as Example 4 to obtain 820 mg (Yield: 75%) of the pure title compound as a white solid.

m.p.: 131°–134° C.

$^1$H NMR(CDCl$_3$, δ): 1.4(dt, 3H), 3.95(s, 6H), 4.9–5.3(m, 1H), 5.8(s, 1H), 6.0–6.2(m, 1H), 7.3(m, 2H), 7.8(s, 1H), 12.7(s, 1H)

The herbicidal effect of the compound according to the present invention was identified by experiments in greenhouse as described hereinafter.

EXAMPLE 21

Pre-emergence treatment test

To produce a suitable preparation, 1 part by weight of active compound was mixed with 5 parts by weight of acetone and 1 part by weight of alkylarylpolyglycolether as emulsifier and then solubilized. The resulting solution was diluted with water to the desired concentration.

Seeds of the test plants were sown in normal soil and, after 24 hours, the preparation containing the active compound as prepared above was applied. It is expedient to keep constant the amount of water per unit area. In addition, the concentration of the active compound in the preparation is very important. After three weeks, the degree of damage of the plants was rated in % damage in comparison to the development of the untreated control, and the evaluation result was represented as follows:

0%=no action (like untreated control)

20%=trivial effect

70%=herbicidal effect

100%=total destruction (complete withering to death)

EXAMPLE 22

Post-emergence treatment test

A preparation containing the active compound was produced according to the same procedure as Example 21. Test plants which have a height of 5 to 15 cm were sprayed with the above preparation in such a way as to apply the desired amount of the active compound per unit area. The concentration of the active ingredient in solution for spraying was determined in such a way that the desired amount of the active compound can be applied when 2000 L of water was sprayed per hectare. After three weeks, the degree of damage of the plants was rated in % damage in comparison to the development of the untreated control, and the evaluation result was represented as in Example 21.

As a result of test, it could be identified that the compound of formula (I) according to the present invention has an excellent herbicidal activity on monocotyledon or dicotyledon weeds by both pre- and post-emergence treatment.

EXAMPLE 23

Paddy Submerged Test

A small amount of fertilizer was added to a round pot(60 cm or 140 cm) and then the pot was filled with sterilized paddy field soil in paste state up to 5 cm in depth. Seeds of Barnyard grass, Umbrella plant, Day Flower, Mono-choria, Toothcup, Ludwigia, Bulrush, False pimpernel, and perennial bulbs such as Flat-sedge, Arrowhead were mixed or sown in a surface layer of the soil and then seedlings (at the stage of 2 to 3 leaves) of the rice plant were planted in a depth of 2 cm from the surface at a population of one root per pot. After transplantation, they were submerged in fresh water at a depth of 2 cm and keeped in such a state for one day. Then, they were uniformly treated by applying dropwise the preparation which was prepared as in Example 21 (4 mg per pot when the applied amount of the preparation is 4 kg/ha). After two weeks, the herbicidal activity was evaluated and the result was represented according to the same criteria as in Example 21.

In the present invention, the herbicidal activities of the active compounds used in the pre- and post-emergence treatment tests according to Examples 21 and 22 are represented in the following Tables 4, 5 and 6.

TABLE 4

TEST FOR DETERMINATION OF EFFECTIVE CONCENTRATION(HERBICIDE)-Water in paddy field

| Camp. No. | Appl. Time | Appl. Conc. (kg/ha) | A | B | C | D | E | F | G |
|---|---|---|---|---|---|---|---|---|---|
| 1 | 2 | .05 | 95 | 100 | 100 | 100 | 100 | 100 | 100 |
|   |   | .0125 | 95 | 95 | 100 | 90 | 100 | 100 | 100 |
|   |   | .00312 | 60 | 90 | 75 | 90 | 95 | 100 | 95 |
| 4 | 2 | .05 | 95 | 100 | 100 | 100 | 100 | 100 | 100 |
|   |   | .0125 | 95 | 95 | 95 | 90 | 100 | 100 | 100 |
| 7 | 2 | .05 | 90 | 100 | 100 | 100 | 100 | 100 | 100 |
|   |   | .0125 | 80 | 100 | 90 | 90 | 100 | 100 | 100 |
|   |   | .00312 | 30 | 60 | 0 | 90 | 85 | 100 | 100 |
|   |   | .00078 | 0 | 0 | 0 | 80 | 30 | 95 | 90 |
| 8 | 2 | .05 | 95 | 100 | 100 | 100 | 100 | 100 | 100 |
|   |   | .0125 | 80 | 90 | 90 | 100 | 100 | 100 | 100 |
|   |   | .00312 | 20 | 70 | 40 | 90 | 80 | 70 | 90 |
|   |   | .00078 | 0 | 0 | 0 | 90 | 0 | 0 | 90 |
| 30 | 2 | .05 | 80 | 100 | 100 | 100 | 100 | 100 | 100 |
|   |   | .0125 | 50 | 80 | 100 | 100 | 80 | 100 | 80 |
| 31 | 2 | .05 | 80 | 100 | 100 | 100 | 100 | 100 | 100 |
|   |   | .0125 | 60 | 80 | 95 | 100 | 90 | 100 | 100 |
|   |   | .00312 | 20 | 60 | 70 | 100 | 95 | 100 | 100 |
| 32 | 2 | .05 | 50 | 80 | 100 | 100 | 90 | 100 | 100 |
|   |   | .0125 | 0 | 40 | 50 | 90 | 60 | 90 | 90 |
| 43 | 2 | .05 | 95 | 100 | 100 | 100 | 100 | 100 | 100 |
|   |   | .0125 | 50 | 70 | 100 | 100 | 80 | 85 | 90 |
| 44 | 2 | .05 | 40 | 70 | 100 | 100 | 90 | 80 | 100 |
|   |   | .0125 | 0 | 20 | 30 | 90 | 60 | 40 | 90 |
| 48 | 2 | .05 | 50 | 100 | 100 | 100 | 100 | 90 | 100 |
|   |   | .0125 | 20 | 50 | 60 | 100 | 60 | 30 | 90 |
| 49 | 2 | .05 | 80 | 100 | 100 | 100 | 100 | 100 | 100 |
|   |   | .0125 | 40 | 50 | 100 | 100 | 100 | 60 | 100 |
| 50 | 2 | .05 | 50 | 100 | 100 | 100 | 100 | 89 | 100 |
|   |   | .0125 | 10 | 30 | 60 | 90 | 100 | 30 | 100 |
| 51 | 2 | .05 | 70 | 90 | 100 | 100 | 100 | 100 | 100 |
|   |   | .0125 | 30 | 40 | 70 | 100 | 100 | 100 | 100 |

TABLE 4-continued

TEST FOR DETERMINATION OF EFFECTIVE CONCENTRATION(HERBICIDE)-Water in paddy field

| Comp. No. | Appl. Time | Appl. Conc. (kg/ha) | A | B | C | D | E | F | G |
|---|---|---|---|---|---|---|---|---|---|
| 52 | 2 | .05 | 70 | 100 | 100 | 100 | 100 | 100 | 100 |
|  |  | .0125 | 50 | 90 | 100 | 100 | 100 | 100 | 100 |
|  |  | .00312 | 0 | 30 | 30 | 90 | 90 | 100 | 100 |
| 53 | 2 | .05 | 65 | 100 | 100 | 100 | 100 | 100 | 100 |
|  |  | .0125 | 20 | 40 | 90 | 100 | 100 | 100 | 100 |
|  |  | .00312 | 0 | 0 | 0 | 40 | 100 | 70 | 100 |
| 76 | 2 | .05 | 80 | 90 | 100 | 100 | 100 | 100 | 100 |
|  |  | .0125 | 30 | 50 | 10 | 90 | 80 | 50 | 90 |
| 77 | 2 | .05 | 70 | 100 | 90 | 100 | 100 | 100 | 100 |
|  |  | .0125 | 30 | 80 | 10 | 90 | 90 | 80 | 90 |
| 82 | 2 | .5 | 100 | 100 | 100 | 100 | 100 | 100 | 100 |
|  |  | .125 | 90 | 100 | 100 | 100 | 100 | 100 | 100 |
|  |  | .03125 | 80 | 90 | 100 | 100 | 100 | 100 | 100 |
|  |  | .00781 | 60 | 80 | 100 | 90 | 100 | 90 | 100 |
| 112 | 2 | .05 | 70 | 70 | 70 | 90 | 90 | 100 | 100 |
|  |  | .1 | 100 | 100 | 100 | 100 | 100 |  | 90 |
|  |  | .025 | 80 | 70 | 50 | 80 | 80 |  | 60 |
| 113 | 2 | .05 | 90 | 100 | 80 | 100 | 100 | 100 | 100 |
|  | 1 | .1 | 100 | 100 | 100 | 100 | 100 |  | 100 |
|  |  | .025 | 100 | 90 | 90 | 100 | 100 |  | 100 |
| 120 | 2 | .05 | 60 | 60 | 90 | 70 |  | 90 | 80 |
|  |  | .05 | 40 | 70 | 90 | 90 | 80 | 70 | 80 |
| 98 | 2 | .05 | 40 | 40 | 50 | 40 | 90 | 100 | 90 |
|  |  | .05 | 30 | 60 | 70 | 90 | 90 | 50 | 90 |
| 99 | 2 | .05 | 75 | 100 | 100 | 100 | 100 | 100 | 100 |
|  |  | .0125 | 40 | 60 | 50 | 90 | 60 | 80 | 80 |

Note:
1) Application Time 1 = pre-emergence
2 = post-emergence
2) A: Rice plant (at the stage of 3 leaves)
B: Rice plant
C: Barnyard grass
D: Bulrush
E: Monochoria
F: Flat-sedge
G: Arrowhead

TABLE 5

TEST ON HERBICIDAL EFFECT

| Comp. No. | Application Time | Appl. Conc. (kg/ha) | H | C | I | J | K | L | M | N | O | P |
|---|---|---|---|---|---|---|---|---|---|---|---|---|
| 2 | pre-emergence | .05 | 80 | 100 | 25 | 85 | 85 | 60 | 30 | 65 | 70 | 90 |
|  | post-emergence | .05 | 60 | 90 | 15 | 55 | 75 | 20 | 15 | 40 | 40 | 70 |
| 3 | pre-emergence | .05 | 65 | 60 | 0 | 25 | 60 | 15 | 0 | 0 | 0 |  |
|  | post-emergence | .05 | 50 | 60 | 10 | 0 | 10 | 15 | 0 | 0 | 0 | 25 |
| 5 | pre-emergence | .05 | 85 | 100 | 15 | 100 | 100 | 50 | 20 | 65 | 75 | 95 |
|  | post-emergence | .05 | 65 | 100 | 15 | 55 | 100 | 20 | 15 | 25 | 30 | 90 |
| 6 | pre-emergence | .05 | 60 | 40 | 0 | 45 | 70 | 45 | 0 | 0 | 0 | 0 |
|  | post-emergence | .05 | 30 | 60 | 0 | 0 | 0 | 10 | 0 | 0 | 0 | 0 |
| 35 | pre-emergence | .05 | 100 | 90 | 0 | 40 | 60 | 60 | 0 | 40 | 60 | 100 |
|  | post-emergence | .05 | 70 | 80 | 0 | 40 | 50 | 60 | 40 | 0 | 100 | 100 |
| 57 | pre-emergence | .05 | 85 | 30 | 0 | 20 | 15 | 0 | 0 | 0 | 0 | 15 |
|  | post-emergence | .05 | 65 | 10 | 0 | 0 | 0 | 15 | 0 | 0 | 30 | 15 |
| 58 | pre-emergence | .05 | 90 | 60 | 10 | 60 | 60 | 10 | 0 | 10 | 65 | 65 |
|  | post-emergence | .05 | 65 | 50 | 10 | 0 | 15 | 0 | 0 | 0 | 20 | 60 |
| 75 | pre-emergence | .05 | 60 | 100 | 40 | 50 | 70 | 30 | 20 | 0 | 80 | 90 |
|  | post-emergence | .05 | 60 | 40 | 20 | 0 | 60 | 80 | 0 | 0 | 90 | 60 |
| 76 | pre-emergence | .05 | 100 | 100 | 80 | 100 | 100 | 70 | 70 | 70 | 100 | 100 |
|  | post-emergence | .05 | 70 | 100 | 60 | 50 | 100 | 40 | 60 | 20 | 100 | 80 |
| 77 | pre-emergence | .05 | 90 | 100 | 60 | 100 | 90 | 50 | 40 | 90 | 90 | 100 |
|  | post-emergence | .05 | 90 | 100 | 60 | 60 | 100 | 60 | 70 | 60 | 100 | 90 |
| 81 | pre-emergence | .05 | 100 | 100 | 80 | 100 | 100 | 80 | 60 | 60 | 90 | 90 |
|  | post-emergence | .05 | 60 | 100 | 40 | 40 | 100 | 100 | 40 | 0 | 70 | 100 |
| 120 | pre-emergence | .05 | 100 | 100 | 0 | 50 | 70 | 40 | 40 | 60 | 80 | 100 |
|  | post-emergence | .05 | 70 | 80 | 0 | 50 | 20 | 0 | 40 | 0 | 90 | 80 |

TABLE 5-continued

TEST ON HERBICIDAL EFFECT

| Comp. No. | Application Time | Appl. Conc. (kg/ha) | H | C | I | J | K | L | M | N | O | P |
|---|---|---|---|---|---|---|---|---|---|---|---|---|
| 96 | pre-emergence | .05 | 70 | 70 | 0 | 100 | 60 | 60 | 50 | 50 | 80 | 90 |
|  | post-emergence | .05 | 70 | 50 | 0 | 30 | 20 | 20 | 0 | 0 | 80 | 60 |
| 97 | pre-emergence | .05 | 80 | 90 | 60 | 100 | 100 | 80 | 60 | 70 | 90 | 100 |
|  | post-emergence | .05 | 80 | 50 | 0 | 20 | 70 | 0 | 0 | 0 | 60 | 50 |
| 123 | pre-emergence | .05 | 60 | 80 | 0 | 100 | 90 | 70 | 0 | 50 | 80 | 100 |
|  | post-emergence | .05 | 80 | 50 | 0 | 20 | 80 | 50 | 0 | 0 | 80 | 70 |
| 98 | pre-emergence | .05 | 30 | 30 | 0 | 60 | 60 | 60 | 0 | 0 | 80 | 100 |
|  | post-emergence | .05 | 70 | 50 | 0 | 0 | 60 | 30 | 30 | 0 | 70 | 50 |
| 99 | pre-emergence | .05 | 90 | 70 | 0 | 100 | 90 | 70 | 70 | 70 | 80 | 100 |
|  | post-emergence | .05 | 80 | 70 | 0 | 0 | 70 | 30 | 40 | 60 | 80 | 50 |

Note:
H: Sorghum
C: Barnyard grass
I: Quackgrass
J: Larger carb-grass
K: American panicum
L: Black nightshade
M: Indian Joint vetch
N: Abutilon avicennae
O: Cocklebur
P: Bindweed

TABLE 6

TEST ON HERBICIDAL EFFECT

| Comp. No. | Appl. Time | Appl. Conc. (kg/ha) | Q | R | S | T | U | H | C | I | J | K | L | M | N | O | P |
|---|---|---|---|---|---|---|---|---|---|---|---|---|---|---|---|---|---|
| 1 | pre- | .1 | 100 | 100 | 100 | 100 | 100 | 100 | 100 | 100 | 100 | 100 | 100 | 100 | 100 | 100 | 100 |
|  | emer | .025 | 100 | 100 | 100 | 60 | 100 | 100 | 100 | 80 | 100 | 100 | 90 | 80 | 90 | 100 | 100 |
|  | gence | .006 | 40 | 70 | 90 | 30 | 100 | 100 | 100 | 50 | 100 | 100 | 90 | 60 | 80 | 90 | 100 |
|  | post- | .1 | 100 | 100 | 80 | 70 | 100 | 100 | 100 | 80 | 60 | 100 | 80 | 100 | 100 | 100 | 100 |
|  | emer | .025 | 60 | 100 | 50 | 30 | 90 | 100 | 100 | 70 | 40 | 100 | 70 | 60 | 100 | 100 | 100 |
|  | gence | .006 | 0 | 100 | 20 | 0 | 30 | 90 | 90 | 50 | 0 | 100 | 20 | 20 | 60 | 70 | 50 |
| 4 | pre- | .1 | 100 | 100 | 100 | 80 | 100 | 100 | 100 | 100 | 100 | 100 | 100 | 100 | 100 | 100 | 100 |
|  | emer | .025 | 100 | 90 | 90 | 30 | 100 | 100 | 100 | 70 | 100 | 100 | 100 | 60 | 100 | 100 | 100 |
|  | gence | .006 | 100 | 70 | 80 | 20 | 100 | 100 | 100 | 60 | 100 | 100 | 90 | 60 | 80 | 90 | 100 |
|  | post- | .1 | 100 | 100 | 80 | 60 | 100 | 100 | 100 | 70 | 60 | 100 | 60 | 100 | 100 | 100 | 100 |
|  | emer | .025 | 90 | 100 | 60 | 40 | 80 | 100 | 100 | 70 | 30 | 100 | 50 | 60 | 100 | 100 | 100 |
|  | gence | .006 | 0 | 90 | 30 | 20 | 40 | 70 | 60 | 40 | 0 | 100 | 0 | 0 | 60 | 70 | 70 |
| 7 | pre- | .1 | 60 | 80 | 90 | 40 | 100 | 100 | 100 | 40 | 100 | 100 | 70 | 60 | 80 | 100 | 100 |
|  | emer | .025 | 50 | 70 | 80 | 20 | 100 | 90 | 100 | 30 | 80 | 100 | 60 | 50 | 70 | 100 | 90 |
|  | gence | .00625 | 0 | 50 | 70 | 0 | 70 | 60 | 80 | 0 | 50 | 100 | 40 | 30 | 60 | 90 | 90 |
|  | post- | .1 | 60 | 100 | 60 | 40 | 80 | 100 | 100 | 80 | 65 | 100 | 70 | 80 | 70 | 100 | 100 |
|  | emer | .025 | 50 | 90 | 30 | 30 | 70 | 90 | 100 | 30 | 40 | 100 | 60 | 70 | 60 | 80 | 90 |
|  | gence | .00625 | 40 | 70 | 0 | 0 | 50 | 50 | 70 | 0 | 0 | 50 | 30 | 30 | 40 | 70 | 50 |
| 8 | pre- | .1 | 100 | 100 | 90 | 90 | 100 | 100 | 100 | 100 | 100 | 100 | 80 | 90 | 80 | 100 | 100 |
|  | emer | .025 | 70 | 80 | 80 | 60 | 100 | 100 | 100 | 60 | 100 | 100 | 50 | 70 | 100 | 100 | 100 |
|  | gence | .00625 | 60 | 60 | 60 | 20 | 90 | 80 | 100 | 30 | 80 | 90 | 50 | 40 | 60 | 90 | 100 |
|  | post- | .1 | 100 | 100 | 100 | 60 | 100 | 100 | 100 | 80 | 100 | 100 | 30 | 80 | 70 | 100 | 100 |
|  | emer | .025 | 70 | 100 | 50 | 40 | 80 | 60 | 100 | 40 | 40 | 90 | 0 | 40 | 50 | 90 | 100 |
|  | gence | .00625 | 0 | 60 | 30 | 0 | 60 | 40 | 70 | 0 | 30 | 20 | 0 | 0 | 0 | 70 | 80 |
| 26 | pre- | .1 | 100 | 90 | 90 | 100 | 100 | 90 | 100 | 90 | 100 | 90 | 70 | 60 | 60 | 100 | 100 |
|  | emer | .025 | 70 | 70 | 80 | 50 | 100 | 80 | 100 | 70 | 90 | 80 | 60 | 40 | 0 | 80 | 100 |
|  | gence | .00625 | 50 | 30 | 0 | 0 | 80 | 70 | 100 | 40 | 50 | 70 | 40 | 20 | 0 | 70 | 100 |
|  | post- | .1 | 60 | 100 | 60 | 40 | 100 | 60 | 100 | 40 | 40 | 70 | 0 | 50 | 0 | 60 | 40 |
|  | emer | .025 | 20 | 100 | 30 | 40 | 70 | 40 | 90 | 20 | 30 | 40 | 0 | 30 | 0 | 60 | 0 |
|  | gence | .00625 | 0 | 50 | 0 | 0 | 20 | 0 | 30 | 0 | 20 | 30 | 0 | 0 | 0 | 0 | 0 |
| 32 | pre- | .1 | 90 | 70 | 100 | 0 | 100 | 100 | 100 | 40 | 100 | 90 | 60 | 80 | 70 | 90 | 100 |
|  | emer | .025 | 60 | 50 | 100 | 0 | 100 | 90 | 100 | 30 | 60 | 90 | 60 | 60 | 60 | 80 | 100 |
|  | gence | .00625 | 50 | 40 | 50 | 0 | 80 | 40 | 65 | 0 | 30 | 60 | 40 | 20 | 20 | 80 | 100 |
|  | post- | .1 | 90 | 100 | 50 | 0 | 50 | 70 | 100 | 40 | 40 | 80 | 40 | 90 | 40 | 100 | 80 |
|  | emer | .025 | 70 | 100 | 20 | 0 | 30 | 50 | 90 | 0 | 20 | 70 | 30 | 80 | 30 | 100 | 40 |
|  | gence | .00625 | 20 | 70 | 0 | 0 | 0 | 40 | 30 | 0 | 0 | 40 | 0 | 0 | 0 | 70 | 20 |
| 44 | pre- | 1 | 100 | 90 | 80 | 20 | 100 | 100 | 100 | 60 | 100 | 90 | 65 | 70 | 70 | 100 | 100 |
|  | emer | .025 | 100 | 50 | 70 | 0 | 90 | 90 | 100 | 30 | 100 | 90 | 50 | 40 | 40 | 100 | 100 |
|  | gence | .00625 | 30 | 30 | 60 | 0 | 65 | 60 | 80 | 0 | 60 | 50 | 30 | 0 | 20 | 100 | 100 |
|  | post- | .1 | 100 | 100 | 70 | 0 | 40 | 80 | 100 | 40 | 50 | 80 | 30 | 70 | 40 | 100 | 100 |

TABLE 6-continued

TEST ON HERBICIDAL EFFECT

| Comp. No. | Appl. Time | Appl. Conc. (kg/ha) | Q | R | S | T | U | H | C | I | J | K | L | M | N | O | P |
|---|---|---|---|---|---|---|---|---|---|---|---|---|---|---|---|---|---|
| | emer | .025 | 70 | 70 | 60 | 0 | 20 | 30 | 80 | 0 | 40 | 70 | 20 | 40 | 30 | 90 | 80 |
| | gence | .00625 | 20 | 40 | 30 | 0 | 0 | 0 | 70 | 0 | 20 | 30 | 0 | 20 | 0 | 80 | 30 |
| 47 | pre-emer | .2 | 100 | 90 | 90 | 40 | 100 | 100 | 100 | 50 | 100 | 100 | 60 | 70 | 100 | 100 | 100 |
| | emer | .05 | 100 | 70 | 80 | 30 | 100 | 100 | 100 | 30 | 100 | 100 | 40 | 30 | 100 | 100 | 100 |
| | gence | .0125 | 40 | 60 | 60 | 0 | 60 | 60 | 100 | 0 | 100 | 90 | 20 | 0 | 50 | 100 | 100 |
| | post-emer | .2 | 100 | 80 | 90 | 50 | 60 | 100 | 100 | 40 | 100 | 100 | 60 | 100 | 100 | 100 | 100 |
| | emer | 05 | 80 | 70 | 70 | 0 | 40 | 100 | 100 | 0 | 50 | 70 | 40 | 50 | 80 | 90 | 100 |
| | gence | .0125 | 0 | 30 | 40 | 0 | 0 | 30 | 60 | 0 | 0 | 40 | 0 | 0 | 40 | 70 | 40 |
| 48 | pre-emer | .2 | 100 | 100 | 100 | 80 | 100 | 100 | 100 | 80 | 100 | 100 | 100 | 90 | 100 | 100 | 100 |
| | emer | .05 | 100 | 80 | 100 | 50 | 100 | 100 | 100 | 60 | 100 | 100 | 90 | 80 | 80 | 100 | 100 |
| | gence | .0125 | 80 | 70 | 60 | 0 | 100 | 90 | 100 | 40 | 100 | 90 | 80 | 50 | 80 | 100 | 100 |
| | post-emer | .2 | 100 | 100 | 100 | 60 | 100 | 100 | 100 | 65 | 100 | 100 | 60 | 100 | 90 | 100 | 100 |
| | emer | 05 | 90 | 100 | 90 | 50 | 100 | 90 | 100 | 60 | 60 | 90 | 50 | 100 | 80 | 100 | 100 |
| | gence | .0125 | 60 | 80 | 80 | 30 | 70 | 60 | 80 | 40 | 30 | 80 | 20 | 80 | 60 | 100 | 100 |
| 49 | pre-emer | .2 | 100 | 90 | 90 | 60 | 100 | 100 | 100 | 70 | 100 | 100 | 60 | 90 | 100 | 100 | 100 |
| | emer | .05 | 100 | 70 | 90 | 40 | 100 | 100 | 100 | 60 | 100 | 90 | 50 | 65 | 70 | 100 | 100 |
| | gence | .0125 | 60 | 50 | 70 | 0 | 80 | 80 | 100 | 40 | 90 | 50 | 40 | 40 | 20 | 90 | 100 |
| | post-emer | .2 | 100 | 100 | 90 | 50 | 70 | 100 | 100 | 60 | 100 | 100 | 60 | 70 | 100 | 100 | 90 |
| | emer | .05 | 100 | 90 | 70 | 30 | 60 | 100 | 100 | 30 | 50 | 100 | 40 | 60 | 60 | 100 | 80 |
| | gence | .0125 | 40 | 40 | 60 | 0 | 40 | 60 | 60 | 0 | 0 | 40 | 0 | 0 | 20 | 80 | 40 |
| 51 | pre-emer | .2 | 100 | 100 | 100 | 40 | 100 | 100 | 100 | 70 | 100 | 100 | 90 | 80 | 90 | 100 | 100 |
| | emer | .05 | 90 | 90 | 100 | 30 | 100 | 100 | 100 | 40 | 100 | 100 | 80 | 70 | 80 | 90 | 90 |
| | gence | .0125 | 65 | 65 | 60 | 0 | 90 | 90 | 100 | 0 | 70 | 100 | 70 | 40 | 60 | 90 | 90 |
| | post-emer | .2 | 100 | 100 | 60 | 50 | 100 | 100 | 100 | 70 | 70 | 100 | 100 | 100 | 100 | 100 | 100 |
| | emer | .05 | 90 | 100 | 50 | 20 | 90 | 100 | 100 | 50 | 50 | 100 | 50 | 100 | 90 | 100 | 100 |
| | gence | .0125 | 80 | 100 | 30 | 0 | 50 | 70 | 90 | 0 | 30 | 100 | 20 | 50 | 50 | 90 | 90 |
| 52 | pre-emer | .2 | 100 | 100 | 100 | 60 | 100 | 100 | 100 | 60 | 100 | 100 | 90 | 100 | 100 | 100 | 100 |
| | emer | .05 | 90 | 90 | 100 | 40 | 100 | 100 | 100 | 40 | 100 | 100 | 80 | 70 | 90 | 100 | 100 |
| | gence | .0125 | 80 | 60 | 90 | 10 | 100 | 90 | 100 | 0 | 90 | 100 | 50 | 60 | 70 | 100 | 100 |
| | post-emer | .2 | 100 | 100 | 90 | 60 | 100 | 100 | 100 | 80 | 90 | 100 | 70 | 100 | 90 | 100 | 100 |
| | emer | .05 | 100 | 100 | 60 | 40 | 80 | 100 | 100 | 70 | 70 | 100 | 50 | 100 | 70 | 100 | 100 |
| | gence | .0125 | 60 | 90 | 40 | 0 | 50 | 90 | 100 | 20 | 40 | 90 | 40 | 90 | 40 | 100 | 100 |
| 53 | pre-emer | .2 | 100 | 70 | 60 | 20 | 100 | 100 | 100 | 20 | 100 | 100 | 60 | 60 | 100 | 100 | 100 |
| | emer gence | .05 | 60 | 60 | 40 | 0 | 100 | 90 | 100 | 0 | 70 | 100 | 50 | 20 | 70 | 100 | 100 |
| | post-emer gence | .2 | 100 | 100 | 60 | 20 | 50 | 100 | 100 | 30 | 60 | 100 | 60 | 100 | 100 | 100 | 100 |
| | | .05 | 80 | 100 | 30 | 0 | 30 | 100 | 100 | 0 | 30 | 80 | 30 | 60 | 100 | 90 | 60 |
| 64 | pre-emer | .1 | 100 | 90 | 90 | 70 | 100 | 100 | 100 | 80 | 100 | 100 | 70 | 90 | 100 | 100 | 100 |
| | emer | .025 | 100 | 80 | 80 | 40 | 100 | 100 | 100 | 60 | 100 | 100 | 50 | 60 | 80 | 100 | 100 |
| | gence | .00625 | 70 | 50 | 60 | 40 | 90 | 90 | 100 | 50 | 100 | 100 | 30 | 20 | 30 | 100 | 100 |
| | post-emer | .1 | 100 | 100 | 90 | 60 | 100 | 100 | 100 | 60 | 100 | 100 | 50 | 100 | 100 | 100 | 100 |
| | emer | .025 | 100 | 70 | 80 | 30 | 90 | 90 | 100 | 20 | 50 | 80 | 20 | 80 | 50 | 100 | 100 |
| | gence | .00625 | 50 | 60 | 60 | 0 | 60 | 40 | 70 | 0 | 20 | 20 | 0 | 30 | 20 | 100 | 40 |
| 66 | pre-emer | .1 | 100 | 100 | 90 | 30 | 100 | 100 | 100 | 60 | 100 | 100 | 70 | 80 | 80 | 100 | 100 |
| | emer | .025 | 80 | 60 | 80 | 20 | 100 | 90 | 100 | 40 | 100 | 100 | 60 | 30 | 70 | 100 | 100 |
| | gence | .00625 | 30 | 30 | 20 | 0 | 60 | 50 | 90 | 20 | 80 | 100 | 50 | 0 | 40 | 100 | 100 |
| | post-emer | .1 | 100 | 100 | 70 | 40 | 100 | 100 | 100 | 40 | 100 | 100 | 70 | 100 | 100 | 100 | 100 |
| | emer | .025 | 70 | 90 | 50 | 20 | 90 | 70 | 100 | 20 | 40 | 90 | 70 | 60 | 70 | 100 | 100 |
| | gence | .00625 | 0 | 70 | 20 | 0 | 50 | 60 | 60 | 0 | 0 | 60 | 20 | 20 | 40 | 80 | 40 |
| 67 | pre-emer | .1 | 100 | 90 | 80 | 40 | 100 | 100 | 100 | 70 | 100 | 100 | 70 | 90 | 90 | 100 | 100 |
| | emer | .625 | 100 | 80 | 70 | 20 | 100 | 100 | 100 | 50 | 100 | 90 | 60 | 60 | 80 | 100 | 100 |
| | gence | .00625 | 40 | 50 | 30 | 0 | 90 | 80 | 100 | 0 | 80 | 80 | 50 | 40 | 30 | 90 | 100 |
| | post-emer | .1 | 100 | 100 | 70 | 40 | 100 | 100 | 100 | 40 | 100 | 100 | 80 | 100 | 100 | 100 | 100 |
| | emer | .025 | 90 | 100 | 60 | 20 | 100 | 100 | 100 | 20 | 50 | 100 | 50 | 70 | 80 | 100 | 60 |
| | gence | .00625 | 60 | 60 | 40 | 0 | 65 | 80 | 90 | 0 | 30 | 100 | 30 | 40 | 40 | 100 | 40 |
| 82 | pre-emer | .1 | 100 | 90 | 100 | 100 | 100 | 100 | 100 | 100 | 100 | 100 | 70 | 80 | 80 | 100 | 100 |
| | emer | .025 | 100 | 70 | 90 | 60 | 100 | 100 | 100 | 80 | 100 | 100 | 60 | 60 | 30 | 80 | 100 |
| | gence | .00625 | 60 | 30 | 40 | 20 | 100 | 70 | 100 | 40 | 60 | 90 | 30 | 0 | 0 | 50 | 100 |
| | post-emer | .1 | 100 | 100 | 80 | 60 | 90 | 70 | 100 | 60 | 70 | 80 | 30 | 80 | 40 | 100 | 100 |
| | emer | .025 | 50 | 100 | 60 | 20 | 80 | 40 | 80 | 40 | 30 | 70 | 20 | 40 | 0 | 90 | 60 |
| | gence | .00625 | 20 | 60 | 30 | 0 | 60 | 0 | 50 | 0 | 0 | 40 | 0 | 0 | 0 | 30 | 20 |
| 111 | pre-emer | .1 | 70 | 60 | 40 | 70 | 100 | 100 | 100 | 100 | 100 | 100 | 70 | 20 | 0 | 100 | 100 |
| | emer gence | .05 | 60 | 20 | 0 | 60 | 100 | 100 | 100 | 100 | 100 | 100 | 60 | 0 | 0 | 50 | 100 |
| | post-emer gence | .1 | 100 | 50 | 20 | 20 | 100 | 100 | 100 | 50 | 100 | 100 | | 40 | 20 | 80 | 100 |
| | | .05 | 40 | 40 | 0 | 0 | 100 | 80 | 100 | 40 | 80 | 100 | | 20 | 0 | 65 | 100 |
| 112 | pre-emer | .1 | 100 | 100 | 100 | 100 | 100 | 100 | 100 | 100 | 100 | 100 | 70 | 100 | 100 | 100 | 100 |
| | emer | .05 | 100 | 100 | 100 | 100 | 100 | 100 | 100 | 100 | 100 | 100 | 50 | 100 | 100 | 100 | 100 |
| | gence | .025 | 100 | 100 | 100 | 65 | 100 | 100 | 100 | 100 | 100 | 100 | 40 | 70 | 80 | 100 | 100 |
| | post-emer | .1 | 100 | 100 | 100 | 100 | 100 | 100 | 100 | 100 | 100 | 100 | | 100 | 100 | 100 | 100 |
| | emer | .05 | 100 | 100 | 100 | 65 | 100 | 100 | 100 | 100 | 100 | 100 | | 100 | 100 | 100 | 100 |

TABLE 6-continued

TEST ON HERBICIDAL EFFECT

| Comp. No. | Appl. Time | Appl. Conc. (kg/ha) | Q | R | S | T | U | H | C | I | J | K | L | M | N | O | P |
|---|---|---|---|---|---|---|---|---|---|---|---|---|---|---|---|---|---|
| | gence | .025 | 100 | 100 | 90 | 30 | 100 | 90 | 100 | 100 | 100 | 100 | | 80 | 40 | 90 | 60 |
| 113 | pre- | .1 | 100 | 100 | 100 | 60 | 100 | 100 | 100 | 100 | 100 | 100 | 50 | 100 | 100 | 100 | 100 |
| | emer | .05 | 100 | 100 | 100 | 40 | 100 | 100 | 100 | 100 | 100 | 100 | 40 | 100 | 100 | 100 | 100 |
| | gence | .025 | 90 | 100 | 70 | 20 | 100 | 100 | 100 | 100 | 100 | 100 | 30 | 50 | 100 | 100 | 100 |
| | post- | .1 | 100 | 100 | 70 | 60 | 100 | 100 | 100 | 100 | 100 | 100 | | 100 | 100 | 100 | 100 |
| | emer | .05 | 100 | 100 | 60 | 40 | 100 | 100 | 100 | 90 | 100 | 100 | | 100 | 100 | 100 | 100 |
| | gence | .025 | 100 | 100 | 60 | 0 | 100 | 100 | 100 | 80 | 70 | 100 | | 100 | 100 | 100 | 90 |

Note:
Q: Corn
R: Bean
S: Cotton
T: Wheat
U: Rice plant
H: Sorghum
C: Barnyard grass
I: Quackgrass
J: Larger carb-grass
K: American panicum
L: Black nightshade
M: Indian joint vetch
N: *Abutilon avicennae*
O: Cocklebur
P: Bindweed

What is claimed is:

1. A thiophenesulfonylurea derivative represented by the following general formula (I):

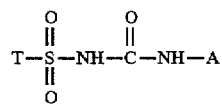
(I)

and a salt thereof, in which

T represents a group T1, T2, or T3 having the following general formula:

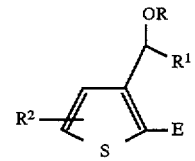
T1

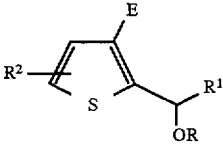
T2

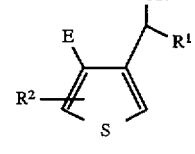
T3 wherein

E represents a direct bond;

R represents hydrogen or $C_{1-4}$ acyl;

$R^1$ represents $C_{1-6}$ alkyl substituted with 1 to 3 halogen atoms;

$R^2$ represents hydrogen, $C_{1-3}$ alkyl, $C_{1-3}$ haloalkyl, halogen, cyano, $C_{1-3}$ alkoxy, $C_{1-3}$ haloalkoxy, amino, methylamino, dimethylamino, or $C_{1-2}$ alkyl substituted with $C_{1-2}$ alkoxy, $C_{1-2}$ haloalkoxy, thiol, methylthio, cyano or hydroxy;

A represents a group selected from the group consisting of A1 to A4 having the following formulae:

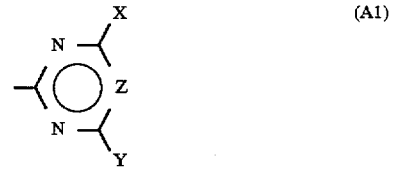
(A1)

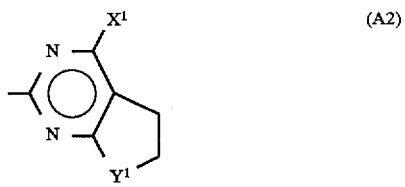
(A2)

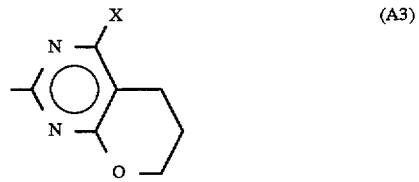
(A3)

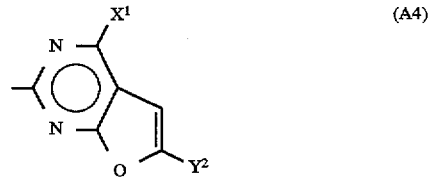
(A4)

wherein

X represents hydrogen, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ haloalkylthio, halogen, $C_{2-5}$ alkoxyalkyl, $C_{2-5}$ alkoxyalkoxy, imino, $C_{1-3}$ alkylamino, di($C_{1-3}$ alkyl)amino or $C_{3-5}$ cycloalkyl;

$X^1$ represents $C_{1-2}$ alkyl, $C_{1-2}$ alkoxy or $C_{1-2}$ alkylthio;

Y represents hydrogen, $C_{1-4}$ alkyl, $C_{1-4}$ alkoxy, $C_{1-4}$ haloalkoxy, $C_{1-4}$ haloalkylthio, $C_{1-4}$ alkylthio, $C_{2-5}$ alkoxyalkyl, $C_{2-5}$ alkoxyalkoxy, amino, $C_{1-3}$ alkylamino, di($C_{1-3}$ alkyl)amino, $C_{3-4}$ alkenyloxy, $C_{3-4}$ alkynyloxy, $C_{2-5}$ alkylthioalkyl, $C_{1-4}$ haloalkyl, $C_{2-4}$ alkynyl, azido, cyano, $C_{2-5}$ alkylsulfinylalkyl, $C_{2-5}$ alkylsulfonylalkyl, hydroxymethyl, $C_{3-5}$ cycloalkyl or $C_{3-5}$ cycloalkoxy;

$Y^1$ represents oxygen or methylene;

$Y^2$ represents hydrogen or methyl; and

Z represents N or CH;

provided that (1) when X is fluoro, chloro, iodo, Z represents CH and Y represents methoxy, ethoxy, methoxymethylamino, amino, methylamino, dimethylamino or difluoromethoxy and (2) when X or Y is difluoromethoxy, Z represents CH and (3) when the total number of carbon atoms of X and Y is 4 or more, $R^2$ represents a group having up to 4 carbon atoms.

2. The compound of formula (I) according to claim 1, wherein T represents T1, T2, or T3 wherein R represents hydrogen or acetyl, $R^1$ represents methyl or ethyl substituted with halogen and $R^2$ represents hydrogen; and A represents A1 wherein X and Y each independently represent $C_{1-4}$ alkyl, $C_{1-4}$ alkoxy or halogen and Z represents N or CH.

3. The compound of formula (I) according to claim 1, wherein T represents T1 wherein R represents hydrogen or acetyl, $R^1$ represents methyl or ethyl substituted with fluorine or chlorine and $R^2$ represents hydrogen; and A represents A1 wherein X and Y each independently represents methyl, methoxy or chloro and Z represents N or CH.

4. The compound of formula (I) according to claim 1, which is N-[(4,6-dimethoxypyrimidin-2-yl)aminocarbonyl]-3-(1-acetoxy-2-fluoroethyl)-2-thiophenesulfonamide.

5. The compound of formula (I) according to claim 1, which is N-[(4,6-dimethoxypyrimidin-2-yl)aminocarbonyl]-3-(1-acetoxy-2-chloroethyl)-2-thiophenesulfonamide.

6. The compound of formula (I) according to claim 1, which is N-[(4,6-dimethoxypyrimidin-2-yl)aminocarbonyl]-3-(1-acetoxy-2-chloropropyl)-2-thiophenesulfonamide.

7. The compound of formula (I) according to claim 1, which is N-[4,6-dimethoxypyrimidin-2-yl)aminocarbonyl]-3-(2-fluoro-1-hydroxyethyl)-2-thiophenesulfonamide.

8. The compound of formula (I) according to claim 1, which is N-[(4,6-dimethoxypyrimidin-2-yl)aminocarbonyl]-3-(1-acetoxy-2-fluropropyl)-2-thiophenesulfonamide.

9. The compound 3-(1-acetoxy-2-fluoroethyl)-2-thiophenesulfonamide.

10. The compound 3-(1-acetoxy-2-chloroethyl)-2-thiophenesulfonamide.

11. The compound 3-(1-acetoxy-2-fluoropropyl)-2-thiophenesulfonamide.

12. A herbicidal composition which contains the compound of formula (I) defined in claim 1 as an active ingredient.

13. The herbicidal composition according to claim 12, which contains the compound of formula (I) wherein T represents T1 wherein R represents hydrogen or acetyl, $R^1$ represents ethyl or propyl substituted with halogen; and A represents A1, as an active ingredient.

14. The herbicidal composition according to claim 12, which contains the compound of formula (I) which is N-[(4,6-dimethoxypyrimidin-2-yl)aminocarbonyl]-3-(1-acetoxy-2-chloroethyl)-2-thiophenesulfonamide as an active ingredient.

15. The herbicidal composition according to claim 12, which contains the compound of formula (I) which is N-[(4,6-dimethoxypyrimidin-2-yl) aminocarbonyl]-3-(1-acetoxy-2-fluoropropyl)-2-thiophenesulfonamide as an active ingredient.

* * * * *